(12) United States Patent
Kamens et al.

(10) Patent No.: US 10,886,008 B2
(45) Date of Patent: Jan. 5, 2021

(54) METHODS AND SYSTEMS FOR DETERMINING THE BIOLOGICAL AGE OF SAMPLES

(71) Applicant: Spring Discovery, Inc., San Carlos, CA (US)

(72) Inventors: Ben Kamens, Palo Alto, CA (US); Ben Komalo, Pittsburgh, PA (US); Wendy Cousin, Belmont, CA (US); Christian Elabd, Belmont, CA (US); Charlie Marsh, New York, NY (US); Lauren Nicolaisen, Redwood City, CA (US)

(73) Assignee: Spring Discovery, Inc., San Carlos, CA (US)

( * ) Notice: Subject to any disclaimer, the term of this patent is extended or adjusted under 35 U.S.C. 154(b) by 0 days.

(21) Appl. No.: 16/255,366

(22) Filed: Jan. 23, 2019

(65) Prior Publication Data

US 2019/0228840 A1 Jul. 25, 2019

Related U.S. Application Data

(60) Provisional application No. 62/621,001, filed on Jan. 23, 2018.

(51) Int. Cl.
*G16B 40/00* (2019.01)
*G16B 20/40* (2019.01)
(Continued)

(52) U.S. Cl.
CPC ........... *G16B 40/00* (2019.02); *C12Q 1/025* (2013.01); *G01N 33/6848* (2013.01);
(Continued)

(58) Field of Classification Search
CPC .......... G06F 40/00; G06F 19/24; G06F 19/12; G06B 45/00; G16B 40/00; G16B 20/00;
(Continued)

(56) References Cited

U.S. PATENT DOCUMENTS

| 2005/0181354 A1* | 8/2005 | Estep, III | G01N 33/5005 435/4 |
| 2011/0196616 A1 | 8/2011 | Gunn | |

(Continued)

FOREIGN PATENT DOCUMENTS

| WO | WO-2012164525 A2 | 12/2012 |
| WO | WO-2014175542 A1 | 10/2014 |
| WO | WO-2017049103 A1 | 3/2017 |

OTHER PUBLICATIONS

Aliper, et al. Deep learning applications for predicting pharmacological properties of drugs and drug repurposing using transcriptomic data. Mol Pharm. Jul. 5, 2016; 13(7): 2524-2530.

(Continued)

*Primary Examiner* — Rebecca M Fritchman
(74) *Attorney, Agent, or Firm* — Wilson Sonsini Goodrich & Rosati

(57) ABSTRACT

The present disclosure provides systems, media, and methods for applying machine learning to determine the biological age of a sample. A method of using a biological age predictor may comprise: (a) providing data of a sample to the biological age predictor; (b) treating the sample with a substance, thereby generating a treated sample; and (c) providing data of the treated sample to the biological age predictor. The biological age predictor may generate the first biological age and/or the second biological age.

30 Claims, 25 Drawing Sheets

(51) Int. Cl.
  *C12Q 1/02* (2006.01)
  *G01N 33/68* (2006.01)
  *G06T 7/00* (2017.01)
  *G16B 20/00* (2019.01)
  *G16B 40/20* (2019.01)

(52) U.S. Cl.
  CPC ............ *G06T 7/0012* (2013.01); *G16B 20/00* (2019.02); *G16B 20/40* (2019.02); *G16B 40/20* (2019.02); *G01N 2500/00* (2013.01); *G01N 2800/7042* (2013.01)

(58) Field of Classification Search
  CPC ................... G16B 20/40; G16B 40/20; G01N 2800/7042; G01N 2500/00; G01N 33/6848; G06T 7/0012; C12Q 1/025
  See application file for complete search history.

(56) References Cited

U.S. PATENT DOCUMENTS

| | | |
|---|---|---|
| 2016/0292380 A1 | 10/2016 | Cho et al. |
| 2017/0342496 A1 | 11/2017 | Zhang et al. |
| 2019/0034581 A1* | 1/2019 | Aliper .................... G16B 40/00 |

OTHER PUBLICATIONS

Cole, et al. Predicting brain age with deep learning from raw imaging data results in a reliable and heritable biomarker. Neuroimage. Dec. 2017;163:115-124.

Conboy, et al. Heterochronic parabiosis for the study of the effects of aging on stem cells and their niches. Cell Cycle vol. 11, 2012—Issue 12: 2260-2267.

Conboy, et al. Rejuvenation of aged progenitor cells by exposure to a young systemic environment. Nature. Feb. 17, 2005;433(7027): 760-4.

D'Orazio, et al. UV radiation and the skin. Int J Mol Sci. Jun. 2013; 14(6): 12222-12248.Published online Jun. 7, 2013.doi: 10.3390/ijms140612222.

Harrison, et al. Rapamycin fed late in life extends lifespan in genetically heterogeneous mice. Nature. Jul. 16, 2009; 460(7253): 392-395.

IDTechEx. AI to accelerate drug discovery for aging and age-associated diseases. Available at https://www.onartificialintelligence.com/journal/print-articles.asp?articleids=11058. Accessed on Jan. 25, 2018.

Phillip, et al. Biophysical and biomolecular determination of cellular age in humans. Nature Biomedical Engineering vol. 1, Article No. 0093 (2017).

Putin, et al. Deep biomarkers of human aging: Application of deep neural networks to biomarker development. Aging (Albany NY). May 2016; 8(5): 1021-1030.

Uno, et al. Lifespan-regulating genes in *C. elegans*. NPJ Aging Mech Dis. 2016; 2: 16010.

Weindruch, et al. The retardation of aging in mice by dietary restriction: longevity, cancer, immunity and lifetime energy intake. J Nutr. Apr. 1986;116(4):641-54.

Deng, et al. ImageNet: A large-scale hierarchical image database. 2009 IEEE Conference on Computer Vision and Pattern Recognition (Jun. 2009), pp. 248-255.

He, et al. Deep Residual Learning for Image Recognition. (Submitted on Dec. 10, 2015); The IEEE Conference on Computer Vision and Pattern Recognition (CVPR), 2016, pp. 770-778.

Kingma, et al. Adam: A Method for Stochastic Optimization. Published as a conference paper at the 3rd International Conference for Learning Representations, San Diego, 2015.

Mark-Anthony, et al. Cell Painting, a high-content image-based assay for morphological profiling using multiplexed fluorescent dyes. Nat Protoc. Sep. 2016; 11(9): 1757-1774.

PCT/US2019/014826 International Search Report and Written Opinion dated Apr. 11, 2019.

* cited by examiner

METHODS AND SYSTEMS FOR DETERMINING THE BIOLOGICAL AGE OF SAMPLES

CROSS-REFERENCE

This application claims the benefit of U.S. Provisional Application No. 62/621,001, filed on Jan. 23, 2018, which is incorporated herein by reference.

BACKGROUND

Aging is among one of the greatest known risk factors for most human diseases. Of the roughly 150,000 people who die each day across the globe, approximately two-thirds die from age-related causes. Aging involves the process of functional deterioration and progressive decline across multiple organs and tissues that arise in part from the progressive accumulation of cellular damage and tissue dysfunction. Such damage and dysfunction to the cells and tissues result in pathophysiological phenotypic transformations.

Aging is a large risk factor for disease and a large driver of healthcare spending. Yet, aging may not be directly treated like most diseases, in part because aging may be assumed to be an unstoppable force. Aging is a complex process and the cause of aging remains unknown. Recently, several attempts have been made to understand the complexities of the aging process. Some studies and evidence may suggest the possibility of factors slowing or reversing cellular aging. While identifying and experimentally validating these factors may lead to a greater understanding of the aging process and the mechanisms involved, such identification and experimental validation can be challenging and require novel computational approaches, especially for the development of effective therapeutics for aging.

SUMMARY

Recognized herein is a need for novel computational approaches to predict the biological age of samples for drug discovery. The present disclosure relates to the phenotypic profiling of the biological age of samples using machine learning. Methods and systems provided herein can significantly increase accuracy of predicting biological age based on analysis of one sample or a combination of two or more samples. Methods and systems provided herein may combine applying machine vision techniques (e.g., machine learning techniques on image data) to sample data (e.g., microscopy image data) to advantageously perform, rapid and low-cost assays for assessing (e.g., predicting) biological age of samples. With increasing evidence that features aging may be visible at the cellular level, applying machine vision to morphological features of cell and/or tissue images to assess biological age of samples may be used as effective screening tools and may be diagnostic for specific disease states (e.g., aging-related diseases). Such morphological features may be extracted and computationally assessed with the use of staining techniques and/or epigenetic assays to reveal morphological predictors of biological age. The methods disclosed herein can be used for drug discovery, especially in identifying an anti-aging agent.

In some aspects, the present disclosure provides a method of using a biological age predictor comprising: (a) providing data of a sample to the biological age predictor, wherein the biological age predictor generates a first biological age; (b) treating the sample with a substance, thereby generating a treated sample; and (c) providing data of the treated sample to the biological age predictor, wherein the biological age predictor generates a second biological age.

In some embodiments, the sample is a cell sample. For example, the cell sample may be a skin, muscle, blood, liver, heart, spleen, thymus, brain, myoblast, fibroblast, or keratinocyte cell sample. In an exemplary embodiment, the cell sample is a skin cell sample. In certain embodiments, the sample is a tissue sample. The tissue sample is a skin, fibroblast, muscle, liver, heart, spleen, thymus, or brain tissue sample. In an exemplary embodiment, the tissue sample is a skin tissue sample.

In some embodiments, the biological age predictor applies machine learning. In some embodiments, the machine learning comprises a convolutional neural network (CNN). In some embodiments, the convolutional neural network comprises a deep convolutional neural network (DCNN). In an embodiment, the biological age predictor is a computer-implemented system, wherein the system has been trained to determine the biological age of the sample. In certain embodiments, the data comprises an image, an epigenetic profile, a proteomic profile, or a metabolomics profile. The data may identify cell morphology, biomarkers, or cellular components.

In some embodiments, the method comprises treating the sample with a substance such as an anti-aging agent. The substance may be a new drug entity.

In some embodiments, the method disclosed herein further comprises comparing the first biological age and the second biological age to determine the efficacy of the substance. In some embodiments, the first biological age or the second biological age of the sample is the specific age of the sample. In another embodiment, the first biological age or the second biological age of the sample is the age range of the sample. In another embodiment, the first biological age and the second biological age of the sample are the relative age of the sample and the treated sample. In some embodiments, the method further comprises staining the sample and the treated sample with a stain. In some embodiments, the method further comprises acquiring a plurality of images of the stained sample to provide the data of the sample, and acquiring a plurality of images of the stained treated sample to provide the data of the treated sample. In some embodiments, the method further comprises processing the plurality of images to determine the first biological age and the second biological age. In some embodiments, the method further comprises determining the first biological age and the second biological age with an accuracy of at least about 80%. In some embodiments, the method further comprises determining a difference in age between the first biological age and the second biological age. In some embodiments, the method further comprises determining a percentage difference in age between the first biological age and the second biological age. In some embodiments, the method further comprises providing a subject in need thereof with the substance, based at least in part on the first biological age and the second biological age.

In some aspects, the present disclosure provides a computer-implemented method of determining the effectiveness of a substance by using a biological age predictor comprising: (a) providing data of a sample to the biological age predictor, wherein the biological age predictor identifies an aging factor; and (b) providing a substance to a subject based on the aging factor.

In some embodiments, the method further comprises providing data of a second sample from the subject subsequent to providing the substance, wherein the biological age predictor applies machine learning to determine the biological age of the second sample. In some embodiments, the biological age predictor applies machine learning.

In some aspects, the present disclosure provides a computer-implemented method of determining the biological age of a sample using a biological age predictor comprising: (a) providing data of a sample to the biological age predictor, wherein the biological age predictor applies machine learning to generate a biological age, wherein providing data of the sample to the biological age predictor does not involve input by a user to identify a feature. In some embodiments, the method further comprises determining the biological age with an accuracy of at least about 80%.

In some aspects, the present disclosure provides a computer-implemented method for determining the biological age of a sample comprising: (a) obtaining a first sample from a first subject; (b) labeling the first sample with a label to generate a labeled sample; (c) performing a first assay on the labeled sample to generate a first sample data; and (d) applying, by a computer comprising a processor configured to execute a computer program including instructions, executable by the processor, to apply a machine learning detection structure to the first sample data, wherein the detection structure employs machine learning to screen locations in the first sample data to: (i) identify a feature and classify the feature to the label; and (ii) determine the biological age of the first sample based at least in part on the identified and classified feature.

In some embodiments, the method further comprises determining the biological age with an accuracy of at least about 80%. In some embodiments, the first sample is a cell sample. The cell sample may be a skin, muscle, blood, liver, heart, spleen, thymus, brain, myoblast, fibroblast, or keratinocyte cell sample. In an exemplary embodiment, the cell sample is a skin cell sample. In some embodiments, the first sample is a tissue sample. The tissue sample may be a fibroblast, skin, muscle, blood, liver, or brain sample. In some embodiments, the first subject is human. In some embodiments, the first subject exhibits a symptom associated with Hutchinson-Gilford Progeria Syndrome (HGPS) or Werner Syndrome. In some embodiments, the first subject exhibits an aging symptom. The aging symptoms may be selected from the group consisting of muscle wasting (sarcopenia), slower wound healing, skin growths, rough skin, dry skin, loose facial skin, transparent skin, decreased skin elasticity, wrinkling, sagging skin, whitening of hair, and graying of hair.

In some embodiments, the first assay comprises staining the first sample. In some embodiments, staining the first sample comprises applying a stain to the first sample, wherein the stains are selected from the group consisting of DAPI, H&E, HES (hematoxylin eosin saffron), Luna stain, Herovici stain, Van Gieson (EVG), and stains used to identify lipofuscin, lysosomes, P16, P19, beta-galactosidase, LC3, ubiquitin, mitochondria, DNA damage, distribution of organelles, nuclear lamina, cell activation, CCR2, soma size, neurites, cytoskeletal structure, or membrane ruffling. In some embodiments, labeling the first sample comprises attributing chronological age, age-related diseases, progression, clinical metadata, or a combination thereof to the first sample. In some embodiments, labeling the first sample comprises attributing information of the first sample by imaging, morphological profiling, cell painting, mass spectrometry, antibody chips, 2-F Fluorescence Difference Gel Electrophoresis (DIGE), mass spectrometric immunoassay (MSIA), or laser capture microdissection (LCM). In some embodiments, the first sample data is an image. In some embodiments, the first sample data is segmented into a plurality of 2D slices, and the detection structure employs the convolutional neural network to screen locations in each of the plurality of 2D slices of the segmented first sample data by a sliding window methodology to identify the feature and classify the feature.

In some embodiments, the method further comprises determining, upon applying the machine learning detection structure to a second sample data obtained from a second assay of a second sample of a second subject, the biological age of the second subject based at least in part on a second feature identified in the second sample data, wherein the feature comprises the second feature. In some embodiments, the first assay and the second assay are the same type of assays. In some embodiments, the first assay and the second assay are different types of assays. In some embodiments, the first sample data and the second sample data are the same type of sample data. In some embodiments, the first sample data and the second sample data are different types of sample data. In some embodiments, the first sample data is image data, proteomics data, or metabolomics data. In some embodiments, the first assay is an epigenetics assay.

In some embodiments, determining the biological age of the first sample comprises determining the specific age of the first sample. In another embodiment, determining the biological age of the first sample comprises determining the age range of the first sample. In another embodiment, determining the biological age of the first sample comprises determining the relative age of the first sample in comparison to the second sample. In some embodiments, the machine learning detection structure comprises a neural network. In certain embodiments, the neural network comprises a convolutional neural network. In certain embodiments, the convolutional neural network comprises a deep convolutional neural network. In some embodiments, the deep convolutional neural network comprises a cascaded deep convolutional neural network.

In some embodiments, the computer program includes instructions, executable by the processor, to apply to the first sample data a network structure selected from the group consisting of recurrent neural network structure and general adversarial network structure. In some embodiments, results from applying the machine learning detection structure are combined with results from applying the network structure to determine the biological age. In some embodiments, the computer program includes instructions, executable by the processor, to apply to the first sample data a technique selected from the group consisting of gradient boosting, random forests, and support vector machines. In some embodiments, results from applying the machine learning detection structure are combined with results from applying the technique.

In some aspects, the present disclosure provides a method of using a biological age predictor comprising: (a) receiving initial data comprising a predicted biological age value from the biological age predictor; (b) automatically labeling the initial data with an extraction program, thereby producing labeled data, wherein the extraction program detects and uniquely labels a desired feature with a first label; and (c) processing the labeled data for use in a second biological age predictor, wherein the second biological age predictor is configured to determine the biological age of a sample subject based at least in part on identification of the desired feature.

In some aspects, the present disclosure provides a computer-implemented system comprising: a digital processing device comprising: (a) a processor; (b) an operating system configured to perform executable instructions; (c) a memory; and (d) a computer program including instructions executable by the digital processing device to create an application applying machine learning detection structures to a plurality of sample data to determine the biological age of a sample, the application comprising: (i) a software module applying a machine learning detection structure to the plurality of sample data, the detection structure employing machine learning to screen locations in the sample to identify a feature and classify the feature; and (ii) a software module automatically generating a report comprising the biological age of a sample from which the sample data was derived.

In some embodiments, the machine learning detection structure comprises a neural network. In some embodiments, the neural network comprises a convolutional neural network. In some embodiments, the convolutional neural network comprises a deep convolutional neural network. In some embodiments, the deep convolutional neural network comprises a cascaded deep convolutional neural network. In some embodiments, the application runs in real-time or near-real time and generates a real-time or near real-time report comprising the biological age of the sample.

In some embodiments, the plurality of sample data is obtained by imaging, morphological profiling, cell painting, mass spectrometry, antibody chips, 2-F Fluorescence Difference Gel Electrophoresis (DIGE), mass spectrometric immunoassay (MSIA), or laser capture microdissection (LCM). In some embodiments, the plurality of sample data is obtained by imaging. In some embodiments, the application further comprises a software module performing image preprocessing comprising normalization of the plurality of the sample data. In some embodiments, the normalization comprises normalization of signal noise, sequencing reads, image channel balancing/combination, quality filtering, color balancing, color normalization, or a combination thereof. In some embodiments, the plurality of sample data comprises image data, and the normalization comprises normalization of image format, image slice spacing, image intensity, image contrast, image saturation, image size, image orientation, or other image data properties of the image data. In some embodiments, the plurality of sample data is segmented into a plurality of 2D slices, and the detection structure employs the convolutional neural network to screen locations in each of the plurality of 2D slices of the segmented sample data by a sliding window methodology to identify the feature and classify the feature.

In some embodiments, the convolutional neural network has 2 to 64 convolutional layers and 1 to 8 fully connected layers. In some embodiments, the sliding window comprises a window of less than about 4,000 pixels by less than about 4,000 pixels. In some embodiments, the sliding window comprises a window of less than about 512 pixels by less than about 512 pixels. In some embodiments, the convolutional neural network comprises a neural network instance selected randomly from a plurality of neural network instances, and the second convolutional neural network comprises a neural network instance selected randomly from a plurality of neural network instances.

In some embodiments, the application further comprises a software module performing post-processing of a plurality of refined locations. In some embodiments, the post-processing comprises characterizing centroid location, volume, shape, intensity, density, transparency, regularity, or a combination thereof. In some embodiments, the report comprises an informational overlay on the sample data. In some embodiments, the report comprises a sample data heat mapped to indicate confidence level. In some embodiments, the report comprises a time course generated by applying the application to medical images captured at two or more time points to measure progression of a disease or growth and movement of a tumor over time. In some embodiments, the machine learning detection structure is trained to identify critical clinical signs of a disease. In some embodiments, the machine learning detection structure is trained using sample data labeled by a human expert and subjected to preprocessing for normalization. In some embodiments, the biological age of the sample comprises a specific age of the sample. In some embodiments, the biological age of the sample comprises an age range of the sample. In some embodiments, the biological age of the sample comprises a relative age of the sample in comparison to an additional sample.

In another aspect, the present disclosure provides a non-transitory computer readable storage medium encoded with a computer program including instructions executable by a processor to create an application applying machine learning to a plurality of sample data to determine the biological age of a sample, the application comprising: (a) a software module applying a machine learning detection structure to the plurality of sample data, the detection structure employing machine learning to screen locations in the plurality of sample data to identify a feature and classify the feature; and (b) a software module automatically generating a report comprising the biological age of a sample from which the sample data was derived.

In some embodiments, the machine learning detection structure comprises a neural network. In some embodiments, the neural network comprises a convolutional neural network. In some embodiments, the convolutional neural network comprises a deep convolutional neural network. In some embodiments, the deep convolutional neural network comprises a cascaded deep convolutional neural network.

In another aspect, the present disclosure provides a high-throughput method of screening a test compound to identify an anti-aging agent, the method comprising: (a) contacting a biological sample with the test compound, thereby generating a treated sample; (b) providing data of the treated sample to a biological age predictor; (c) determining a biological age of the treated sample using a biological age predictor; and (d) identifying the test compound as an anti-aging agent based at least in part on the determined biological age. In some embodiments, the method further comprises identifying the test compound as an anti-aging agent when the determined biological age is a relative reduction relative to a biological age of the biological sample of at least about 10%.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
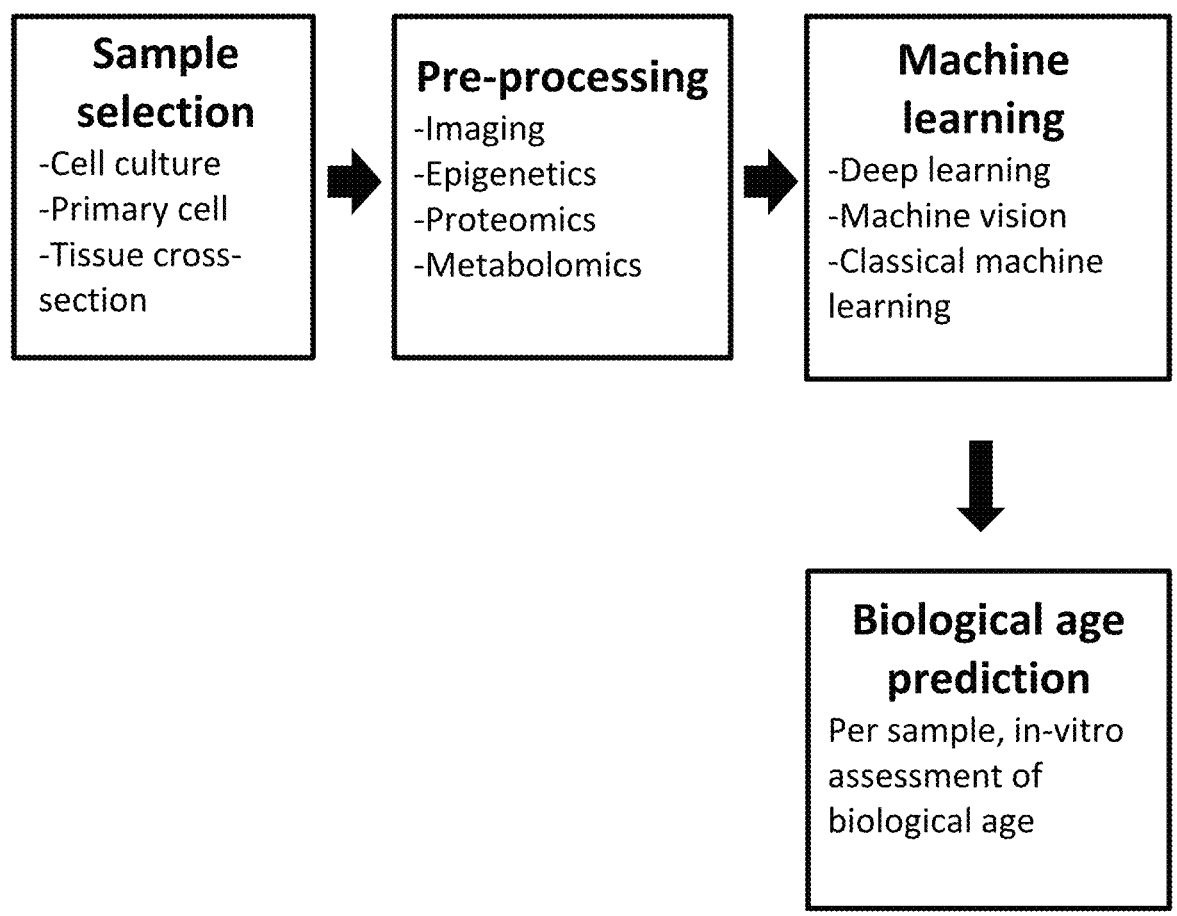
FIG. 1 illustrates an example workflow for predicting the biological age of a sample, including sample selection, pre-processing, machine learning, and biological age prediction, according to disclosed embodiments.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. Unless stated otherwise, the present invention is not limited by the illustrated ordering of acts or events, as some acts may occur in different orders and/or concurrently with other acts or events. Furthermore, not all illustrated acts or events are required to implement a methodology in accordance with the present invention. The concentration of various components in the disclosed compositions is exemplary and not meant to be limited to the recited concentration per se.

It will be understood that a word appearing herein in the singular encompasses its plural counterpart, and a word appearing herein in the plural encompasses its singular counterpart, unless implicitly or explicitly understood or stated otherwise. Further, it will be understood that for any given component described herein, any of the possible candidates or alternatives listed for that component, may generally be used individually or in any combination with one another, unless implicitly or explicitly understood or stated otherwise. Additionally, it will be understood that any list of such candidates or alternatives, is merely illustrative, not limiting, unless implicitly or explicitly understood or stated otherwise. Still further, it will be understood that any figure or number or amount presented herein is approximate, and that any numerical range includes the minimum number and the maximum number defining the range, whether the word "inclusive" or the like is employed or not, unless implicitly or explicitly understood or stated otherwise. Generally, the term "approximately" or "about" or the symbol "~" in reference to a figure or number or amount includes numbers that fall within a range of ±5% of same, unless implicitly or explicitly understood or stated otherwise. Yet further, it will be understood that any heading employed is by way of convenience, not by way of limitation. Additionally, it will be understood that any permissive, open, or open-ended language encompasses any relatively permissive to restrictive language, less open to closed language, or less open-ended to closed-ended language, respectively, unless implicitly or explicitly understood or stated otherwise. Merely by way of example, the word "comprising" may encompass "comprising", "consisting essentially of", and/or "consisting of" type language.

As used herein, unless otherwise indicated, some inventive embodiments herein contemplate numerical ranges. A variety of aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range as if explicitly written out. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. When ranges are present, the ranges include the range endpoints.

Definitions

The term "sample," as used herein, generally refers to a biological sample. The samples may be taken from tissue or cells or from the environment of tissue or cells. In some examples, the sample may comprise, or be derived from, a tissue biopsy, blood, blood plasma, extracellular fluid, dried blood spots, cultured cells, culture media, discarded tissue, plant matter, synthetic proteins, bacterial and/or viral samples, fungal tissue, archaea, or protozoans. The sample may have been isolated from the source prior to collection. Samples may comprise forensic evidence. Non-limiting examples include a finger print, saliva, urine, blood, stool, semen, or other bodily fluids isolated from the primary source prior to collection. In some examples, the sample is isolated from its primary source (cells, tissue, bodily fluids such as blood, environmental samples, etc.) during sample preparation. The sample may be derived from an extinct species including but not limited to samples derived from fossils. The sample may or may not be purified or otherwise enriched from its primary source. In some cases the primary source is homogenized prior to further processing. In some cases, cells are lysed using a buffer such as RIPA buffer. Denaturing buffers may also be used at this stage. The sample may be filtered or centrifuged to remove lipids and particulate matter. The sample may also be purified to remove nucleic acids, or may be treated with RNases or DNases. The sample may contain tissues or cells that are intact, fragmented, or partially degraded.

The sample may be taken from a subject with a disease or disorder. The disease or disorder may be an infectious disease, an immune disorder or disease, a cancer, a genetic disease, a degenerative disease, a lifestyle disease, an injury, a rare disease or an age related disease. The infectious disease may be caused by bacteria, viruses, fungi, and/or parasites. Non-limiting examples of cancers include Bladder cancer, Lung cancer, Brain cancer, Melanoma, Breast cancer, Non-Hodgkin lymphoma, Cervical cancer, Ovarian cancer, Colorectal cancer, Pancreatic cancer, Esophageal cancer, Prostate cancer, Kidney cancer, Skin cancer, Leukemia, Thyroid cancer, Liver cancer, and Uterine cancer. Some examples of genetic diseases or disorders include, but are not limited to, age-related disorders (such as Hutchinson-Gilford Progeria Syndrome (HGPS) or Werner Syndrome), cystic fibrosis, Charcot-Marie-Tooth disease, Huntington's disease, Peutz-Jeghers syndrome, Down syndrome, Rheumatoid arthritis, and Tay-Sachs disease. Non-limiting examples of lifestyle diseases include obesity, diabetes, arteriosclerosis, heart disease, stroke, hypertension, liver cirrhosis, nephritis, cancer, chronic obstructive pulmonary disease (COPD), hearing problems, and chronic backache. Some examples of injuries include, but are not limited to, abrasion, brain injuries, bruising, burns, concussions, congestive heart failure, construction injuries, dislocation, flail chest, fracture, hemothorax, herniated disc, hip pointer, hypothermia, lacerations, pinched nerve, pneumothorax, rib fracture, sciatica, spinal cord injury, tendons ligaments fascia injury, traumatic brain injury, and whiplash. The sample may be taken before and/or after treatment of a subject with a disease or disorder. Samples may be taken before and/or after a treatment. Samples may be taken during a treatment or a treatment regime. Multiple samples may be taken from a subject to monitor the effects of the treatment over time.

The sample may be taken from a subject known or suspected of having an infectious disease for which diagnostic antibodies are not available.

The sample may be taken from a subject suspected of having a disease or a disorder. The sample may be taken from a subject experiencing unexplained symptoms, such as fatigue, nausea, weight loss, aches and pains, weakness, or memory loss. The sample may be taken from a subject having explained symptoms. The sample may be taken from a subject at risk of developing a disease or disorder due to factors such as familial history, age, environmental exposure, lifestyle risk factors, or presence of other known risk factors.

The sample may be taken from an embryo, fetus, or pregnant woman. In some examples, the sample may be isolated from the mother's blood plasma. In some examples, the sample may comprise circulating fetal cells in the mother's blood plasma.

The sample may be taken from a healthy subject. In some cases, samples may be taken longitudinally from the same subject. In some cases, samples acquired longitudinally may be analyzed with the goal of monitoring individual health and early detection of health issues. In some embodiments, the sample may be collected at a home setting or at a point-of-care setting and subsequently transported by a mail delivery, courier delivery, or other transport method prior to analysis. For example, a home user may collect a blood spot sample through a finger prick, which blood spot sample may be dried and subsequently transported by mail delivery prior to analysis. In some cases, samples acquired longitudinally may be used to monitor response to stimuli expected to impact healthy, athletic performance, or cognitive performance. Non-limiting examples include response to medication, dieting, or an exercise regimen. The sample may also be a control.

The sample may be tagged, e.g., with identifiable tags, to allow for multiplexing of samples. Some non-limiting examples of identifiable tags include: fluorophores, magnetic nanoparticles, or DNA barcoded base linkers. Fluorophores used may include fluorescent proteins such as GFP, YFP, RFP, eGFP, mCherry, tdtomato, FITC, Alexa Fluor 350, Alexa Fluor 405, Alexa Fluor 488, Alexa Fluor 532, Alexa Fluor 546, Alexa Fluor 555, Alexa Fluor 568, Alexa Fluor 594, Alexa Fluor 647, Alexa Fluor 680, Alexa Fluor 750, Pacific Blue, Coumarin, BODIPY FL, Pacific Green, Oregon Green, Cy3, Cy5, Pacific Orange, TRITC, Texas Red, Phycoerythrin, Allophcocyanin, or other fluorophores known in the art.

Any number of samples may be multiplexed. For example, a multiplexed analysis may contain samples from 2, 3, 4, 5, 6, 7, 8, 9, 10, 11, 12, 13, 14, 15, 16, 17, 18, 19, about 20, about 25, about 30, about 35, about 40, about 45, about 50, about 55, about 60, about 65, about 70, about 75, about 80, about 85, about 90, about 95, about 100, or more than 100 initial samples. The identifiable tags may provide a way to interrogate each sample as to its origin, or may direct different samples to segregate to different areas or a solid support.

Any number of samples may be mixed prior to analysis without tagging or multiplexing. For example, a multiplexed analysis may contain samples from 2, 3, 4, 5, 6, 7, 8, 9, 10, 11, 12, 13, 14, 15, 16, 17, 18, 19, about 20, about 25, about 30, about 35, about 40, about 45, about 50, about 55, about 60, about 65, about 70, about 75, about 80, about 85, about 90, about 95, about 100, or more than 100 initial samples. Samples may be multiplexed without tagging using a combinatorial pooling design in which samples are mixed into pools in a manner that allows signal from individual samples to be resolved from the analyzed pools using computational demultiplexing.

The term "label," as used herein, generally refers to information that is capable of being analyzed to predict biological age of a sample. The label may be a direct signal indicative of the presence or absence of a cell or tissue. The label may be an indirect signal indicative of the presence or absence of a cell or tissue, such as a fluorescent signal. Labeling may comprise attributing information of one or more samples, such as by imaging, morphological profiling, cell painting, mass spectrometry, antibody chips, 2-F Fluorescence Difference Gel Electrophoresis (DIGE), mass spectrometric immunoassay (MSIA), laser capture microdissection (LCM), or a combination thereof.

Introduction

Aging is a significant problem and represents the major risk factor for most human pathologies including diabetes, cardiovascular diseases, neurological disorders, and cancer. Scientific discoveries over the past two decades have sought to identify molecular mechanisms which play important roles in determining longevity. Such a feat has been challenging since aging is a complex process that involves a number of factors. The present disclosure addresses the need to identify and evaluate such factors across sample types through a machine-learning-driven predictor by determining the biological age of the sample, as well as related features, and thus provide a platform for drug discovery.

The nature of measuring biological age can be very complex and may not be well suited for measuring a single pathway or biomarker. This can pose challenges and difficulties in measuring and quantifying biological aging, especially through in vitro assays that may not be able to measure the functional performance of the subject organism.

For each sample obtained from a subject, sample data may be generated by performing various assays on the sample, or by attributing information (e.g., measurements) of the sample. By performing suitable in vitro assays on samples (e.g., cells and tissue cross sections) obtained from subjects, methods and systems disclosed herein can assess the biological age of the samples using machine learning. Such assays may combine data from a number of different phenotypic sources, such as images of various cell and/or tissue types, each with multiple different stains that are selected to highlight different phenotypic properties; epigenetic and/or gene expression data; and proteomics analysis. For example, such assays may highlight certain morphological features, biomarkers (e.g. telomere length), epigenetic alterations (e.g. DNA methylation patterns, post-transcriptional modification of histones, and chromatin remodeling) and/or components, such as a specific protein, of a sample. Machine learning techniques may be pre-trained to combine sample data obtained from these assays and identify complex, interconnected signals used to determine the biological age of the sample.

Methods and systems described herein may combine applying machine vision techniques (e.g., machine learning techniques on image data) to sample data (e.g., microscopy image data) to advantageously perform, rapid and low-cost assays for assessing (e.g., predicting) biological age of samples. With increasing evidence that aging features may be visible at the cellular level, applying machine vision to morphological features of cell and/or tissue images to assess biological age of samples may be used as effective screening tools and may be diagnostic for specific disease states (e.g., aging-related diseases). Such morphological features may be extracted and computationally assessed with the use of staining techniques and/or epigenetic assays to reveal morphological predictors of biological age.

In particular, methods and systems described herein may have several advantages over other approaches to assess biological age of samples and for biomarker and screening studies in aging-related research, such as unbiased analysis, broad phenotypic coverage through imaging, measurement of complex features, generative hypotheses, rapid assessment, and wide applicability.

Methods and systems described herein may feature unbiased analysis. The machine learning-driven phenotypic approach is an unbiased method of analyzing many features over large quantities of biological data, thereby reducing the need to begin with specific scientific hypotheses in order discover biomarkers or deploy them for drug screens. This may be a significant advantage in aging research and drug development, where quality biomarkers for drug screening may be elusive Methods and systems described herein may feature broad phenotypic coverage through imaging, particularly when combined with high-content imaging. High-content imaging can provide "broad phenotypic coverage" by enabling the measurement of many interrelated biological features at once without requiring a priori knowledge of what features to focus on for imaging. Such broad phenotypic coverage may be particularly advantageous when compared with more specific biomarkers.

Methods and systems described herein may feature a machine learning approach that enables the measurement of extremely complex phenotypic features that are either singularly difficult to quantify (e.g., the complicated shape, structure, and relationships of mitochondria in an image) or are combined into complex sets of features (e.g., the combined features of nuclei, mitochondria, and many specific proteins). This may be a significant advantage over other high-content screening techniques that may tend towards focusing on one or two easily measured features such as cell proliferation Methods and systems described herein may feature generative hypotheses. The unbiased machine learning approach can enable its user to generate hypotheses by allowing the machine to discover correlations, after which models are inspected to understand specific biological changes occurring between populations.

Methods and systems described herein may feature rapid assessment. The machine learning approach can enable biomarker discovery and drug screening analyses to be performed extremely quickly without requiring manual creation of specific biological hypotheses or manual measurement, feature analysis, or analytical coding. These methods can be deployed rapidly, with timeframes from sample acquisition to processing to analysis completed in weeks or less. Once the analysis process is created, future analyses can be performed without requiring customize analytical pipelines, even when experimental parameters like cell types, stains, or compounds are changed.

Methods and systems described herein may feature wide applicability. The machine learning approach can be easily transitioned from one cell type or experimental process to another without requiring new coding or analysis, which are usually needed in other approaches to measure new features or analyze new experimental contexts.

Biological Age Predictor

The present disclosure provides methods and systems of using machine learning to create and train a biological age predictor (e.g., using training datasets). Such biological age predictors may be used to predict the biological age of a given biological sample obtained from a subject.

FIG. 1 illustrates an example workflow for predicting the biological age of a sample, including sample selection, pre-processing, machine learning, and biological age prediction, according to disclosed embodiments. Sample selection may include, for example, preparing cell cultures (e.g., multiple cell types such as skin, muscle, and/or liver obtained from human and/or animal subjects) and/or tissue cross-sections (e.g., multiple tissue types such as skin, muscle, and/or liver obtained from human and/or animal subjects). Samples may be prepared using any number of preparation steps designed to highlight certain features or phenotypic properties that are desired for machine learning detection. For example, in the case of imaging data, samples are prepared using a subset of stains designed to highlight specific morphological features and/or certain components of the sample, such as a specific protein. Additionally, the samples are properly labeled for use during machine learning training. These labels may include chronological age as well as other relevant features like age-related diseases, progression, or relevant clinical metadata (in the case of human samples). Certain features may be automatically labeled using a feature extractor which can detect macro features in the dataset for use by the training algorithm.

Next, the samples may undergo pre-processing in order to generate data using the prepared sample. This can involve any number of data generation steps depending on the sample type and machine learning system that will be used, such as imaging, sequencing, -omics measurements (genomics, proteomics, metabolomics, etc.), or any other distillation of digital data or combination thereof taken from the prepared samples. This raw data may then be combined with the labels to be fed into the machine learning system. Additionally, combinations of transforms may be applied on this raw data for the purpose of data augmentation which aids in generalization for the machine learning process. The pre-processing steps may include, for example, imaging (e.g., by microscopy with specific stain selections and/or automated high-content imaging of cell cultures), epigenetic assays (e.g., gene expression assays), proteomics, and/or metabolomics, thereby generating sample data.

Next, machine learning techniques (e.g., deep learning, machine vision, classical machine learning such as linear regression, and others) may be applied to the generated sample data to combine each sample's multiple data sources. A combination of machine learning techniques may be used to learn from the raw data, such as deep learning, "classical" machine learning (gradient boosting, random forests, support vector machines), and feature engineering to assist those techniques. Models may be built that handle each sample type and its associated preparation process well such that the machine learning system can gradually improve itself via repeated experimentation and evaluation until the resulting models, weights, hyperparameters, and feature extractors are capable of successfully predicting biological age for a given sample. Different sample types and data generation steps may require different machine learning techniques. For example, data produced via imaging may be suitable for machine vision techniques and models to identify correlations and signal in microscopic images. Data produced via epigenetic sequencing may be suitable for genomic machine learning techniques and models. These approaches share underlying fundamentals (for example, both may use optimization methods such as gradient descent), but the technological approaches used may differ depending on the data type (e.g., images vs. sequencing data). Similarly, the exact model structure may differ depending on the source of the sample (e.g., muscle sample vs. liver sample), and the learned weights of the model may differ depending on many of the processes used during data gathering (e.g., which lab and what sets of equipment and workflows were used to acquire, prepare, and process the samples). Over time, these techniques and models may become more generalized and more and more shareable across multiple sample types and preparation processes.

Finally, a machine learning-based biological age predictor may be trained which is capable of taking input from a specific type of biological sample that went through a specific preparatory process, and generating a prediction of its biological age or biological age-associated features (such as disease progression or other macro biological features). The biological age of the sample can be predicted based on a per-sample, in-vitro assessment of biological age using the machine learning outputs.

Figure 2:
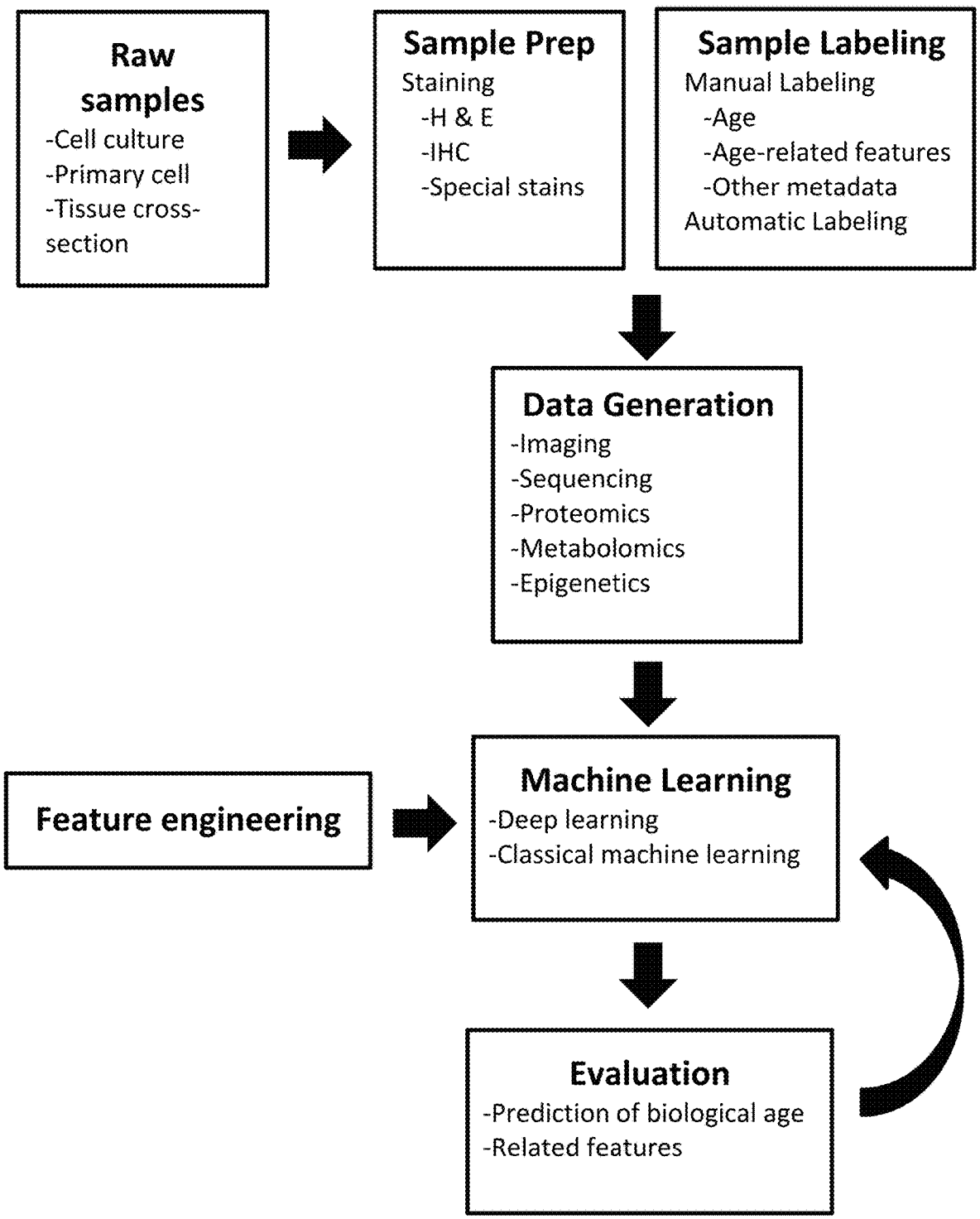
FIG. 2 illustrates a process for creating and training a machine-learning driven predictor for a given sample.

FIG. 2 illustrates a process for creating and training a machine-learning driven predictor for a given sample. Raw samples (e.g., cell cultures, primary cells, and/or tissue cross-sections) may be obtained. The samples may be processed by sample preparation methods, such as staining (e.g., H&E, immunohistochemistry (IHC), special stains, or combinations thereof). The samples may be labeled by manual labeling (e.g., by associating with information such as age, age-related features, or other metadata) or automatic labeling. Data may be generated from the prepared and labeled samples, through assays or other measurement techniques such as imaging, sequencing, proteomics, metabolomics, epigenetics, etc. Machine learning techniques (e.g., deep learning and/or classical machine learning) may be applied to the generated data to create and/or train the machine-learning driven age predictor. For example, a set of features (e.g., found through feature engineering) may be extracted from the generated data for machine learning applications. The machine-learning driven predictor may be evaluated (e.g., for accurate prediction of biological age) and/or features may be refined, possibly through iterative training and machine learning, to improve or optimize predictor accuracy.

Figure 3:
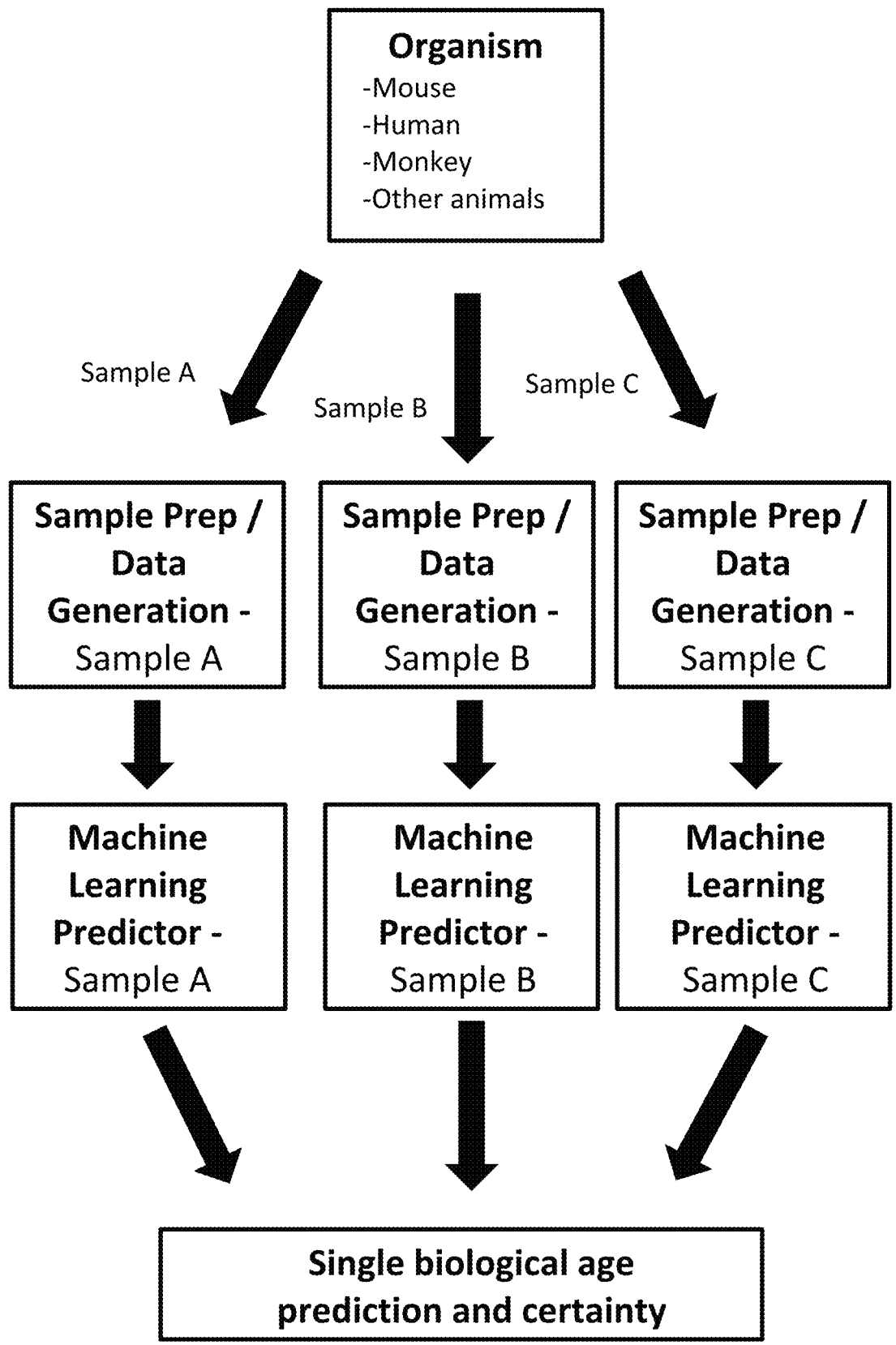
FIG. 3 illustrates a process for using a machine-learning driven predictor to process a plurality of samples to generate a biological age prediction.

FIG. 3 illustrates a process for using a machine-learning driven predictor to process a plurality of samples to generate a biological age prediction. A plurality of samples (e.g., Sample A, Sample B, and Sample C) may be obtained from one or more subject organisms (e.g., mouse, human, monkey, or other animals). Each sample in the plurality of samples may be processed for sample preparation and data generation, as described elsewhere herein. For each sample in the plurality of samples, a machine learning predictor may be created or trained using the sample, and/or applied to the sample. The outputs of the machine learning predictors for the plurality of samples may be processed or combined to generate a single biological age prediction and/or certainty for the plurality of samples. For example, the plurality of biological ages predicted from the plurality of samples may be averaged together to generate the single biological age prediction. As another example, one or more mathematical functions may be applied to the plurality of biological ages predicted from the plurality of samples to generate the single biological age prediction. For example, the maximum or minimum value among the plurality of biological ages predicted from the plurality of samples may be calculated to generate the single biological age prediction.

In an aspect, the present disclosure provides a computer-implemented method for determining the biological age of a sample. The method for determining the biological age of a sample may comprise obtaining a first sample from a first subject. In some embodiments, the first sample is a cell sample. The cell sample may originate from primary cells or cell lines (e.g., grown cell cultures). The cell sample may comprise cells collected from or derived from one or more organs or tissues. For example, the cell sample may be a skin, fibroblast, muscle, blood, liver, heart, spleen, thymus, and/or brain cell sample. In some embodiments, the first sample is a tissue sample (e.g., a tissue cross-section). The tissue sample may comprise tissues collected from or derived from one or more organs or tissues. For example, the tissue sample may be a fibroblast, skin, muscle, blood, liver, and/or brain tissue sample.

Samples may be drawn from subjects such as humans or animals. Subjects may exhibit an aging symptom. Examples of aging symptoms include muscle wasting (sarcopenia), slower wound healing, skin growths, rough skin, dry skin, loose facial skin, transparent skin, decreased skin elasticity, wrinkling, sagging skin, whitening of hair, graying of hair, increased susceptibility to infection, greater risk of heat stroke or hypothermia, decrease in height, increased susceptibility to breaking bones, joint changes, stooped posture, osteoarthritis, frailty, slowed movement, limited movement, decrease in energy, constipation, urinary incontinence, impairment of thought, impairment of memory, impairment of thinking, dementia, reduced reflexes, reduced coordination, increased difficulty with balance, decreased visual acuity, diminished peripheral vision, increase risk for developing presbyopia, hearing loss, decreased fertility, menopause, increased susceptibility to developing atherosclerosis, or weight loss. In particular, aging symptoms such as muscle wasting (sarcopenia), slower wound healing, skin growths, rough skin, dry skin, loose facial skin, transparent skin, decreased skin elasticity, wrinkling, sagging skin, whitening of hair, or graying of hair may be commonly observed in subjects exhibiting aging symptoms. Subjects may exhibit a symptom associated with an age-related disorder, such as Hutchinson-Gilford Progeria Syndrome (HGPS) or Werner Syndrome.

After obtaining the sample from the subject, the method for determining the biological age of a sample may comprise labeling the first sample with a label to generate a labeled sample. Such labels may be used for training the biological age. Samples may be labeled by attributing a set of one or more characteristics to the sample, such as, chronological age, age-related diseases, progression, clinical metadata, or a combination thereof. Samples may be labeled by attributing information (e.g., measurements) of the sample (sample data), which may be obtained by, for example, imaging, morphological profiling, cell painting, mass spectrometry, antibody chips, 2-F Fluorescence Difference Gel Electrophoresis (DIGE), mass spectrometric immunoassay (MSIA), or laser capture microdissection (LCM).

After generating the labeled sample, the method for determining the biological age of a sample may comprise performing a first assay on the labeled sample to generate a first sample data. For example, performing the first assay on the labeled sample may comprise staining the first sample. Examples of stains used to stain samples include DAPI (4',6-Diamidino-2-phenylindole dihydrochloride), H&E (Haemotoxylin and Eosin), HES (hematoxylin eosin saffron), Luna stain, Herovici stain, Van Gieson (EVG), and stains used to identify cellular or sub-cellular features, proteins or other characteristics (e.g., lipofuscin, lysosomes, P16, P19, beta-galactosidase, LC3, ubiquitin, mitochondria, DNA damage, distribution of organelles, nuclear lamina, cell activation, CCR2, soma size, neurites, cytoskeletal structure, or membrane ruffling). Therefore, the sample data (e.g., the first sample data) may comprise staining information of the sample, such as an image. The image data of a sample may be segmented into a plurality of 2D slices, and wherein the detection structure employs the convolutional neural network to screen locations in each of the plurality of 2D slices of the segmented first sample data by a sliding window methodology to identify features and classify the features. As described herein, features may include specific morphological features (e.g. shape, appearance, cell size, nuclear size, nucleolar size, number of multinucleated cells, prominent Golgi apparati, number of vacuoles in the endoplasmic reticulum and cytoplasm, number of cytoplasmic microfilaments, and/or size of lysosomal bodies), or the presence or absence of certain components of the sample, such as a specific protein. In addition to morphology, features may also include IGF-1, EGF, c-fos, senescence-associated-β-galactosidase (SA-β-GAL), senescence-associated heterochromatin foci (SAHF), promyelocytic leukemia protein nuclear bodies (PML NBs), DNA, RNA, chromosome, annexin A5, and an inflammatory secretome.

After generating the first sample data, the method for determining the biological age of a sample may comprise applying, by a computer comprising a processor configured to execute a computer program including instructions, executable by the processor, to apply a machine learning detection structure to the first sample data. The detection structure may employ machine learning to screen locations in the first sample data to identify features and classify the features to the label. Further, the detection structure may employ machine learning to determine the biological age of the first sample based at least in part on the identified and classified features.

In some embodiments, the detection structure may also employ machine learning to determine, upon applying the machine learning detection structure to a second sample data obtained from a second assay of a second sample of a second subject, the biological age of the second subject. The biological age of the second subject may be determined based at least in part on a second feature identified in the second sample data. The features may comprise the second feature. The first assay performed on the first sample of the first subject and the second assay performed on the second sample of the second subject may be the same type of assays. Alternatively, the first assay performed on the first sample of the first subject and the second assay performed on the second sample of the second subject may be different types of assays. For examples, types of assays performed on samples may include staining or an epigenetic assay. The first sample data obtained from the first assay and the second sample data obtained from the second assay may be the same type of sample data (e.g., image data). Alternatively, the first sample data obtained from the first assay and the second sample data obtained from the second assay may be different types of sample data. For example, types of sample data may include image data, proteomics data, or metabolomics data.

The method may determine a biological age of the sample by determining a specific age of the sample, for example, about 1, 2, 3, 4, 5, 6, or 7 days; about 1, 2, 3, or 4 weeks; about 1, 2, 3, 4, 5, 6, 7, 8, 9, 10, 11, or 12 months; or about 1, 2, 3, 4, 5, 6, 7, 8, 9, 10, 15, 20, 25, 30, 35, 40, 45, 50, 55, 60, 65, 70, 75, 80, 85, 90, 95, 100, or more than 100 years. Determining the specific age of a sample may also include determining an expected mean error for the determined specific age, such as about 1, 2, 3, 4, 5, 6, or 7 days; about 1, 2, 3, or 4 weeks; about 1, 2, 3, 4, 5, 6, 7, 8, 9, 10, 11, or 12 months; or about 1, 2, 3, 4, 5, 6, 7, 8, 9, or 10 years. For example, the specific age of a sample may be determined with an expected mean error of no more than about 1, 2, 3, 4, 5, 6, 7, 8, 9, 10, 11, or 12 months; or no more than about 1, 2, 3, 4, 5, 6, 7, 8, 9, or 10 years. Determining the specific age of a sample may also include determining a confidence interval for the determined specific age, such as plus or minus about 1, 2, 3, 4, 5, 6, or 7 days; about 1, 2, 3, or 4 weeks; about 1, 2, 3, 4, 5, 6, 7, 8, 9, 10, 11, or 12 months; or about 1, 2, 3, 4, 5, 6, 7, 8, 9, or 10 years.

The method may determine biological age of the sample by determining an age range of the sample, for example, between about 1-5 years, 5-10 years, 10-15 years, 15-20 years, 20-25 years, 25-30 years, 30-35 years, 35-40 years, 40-45 years, 45-50 years, 50-55 years, 55-60 years, 60-65 years, 65-70 years, 70-75 years, 75-80 years, 80-85 years, 85-90 years, 90-95 years, 95-100 years, 1-10 years, 10-20 years, 20-30 years, 30-40 years, 40-50 years, 50-60 years, 60-70 years, 70-80 years, 80-90 years, or 90-100 years. The method may determine biological age of the sample by determining a relative age of the first sample in comparison to the second sample, for example, about 1, 2, 3, 4, 5, 6, 7, 8, 9, 10, 15, 20, 25, 30, 35, 40, 45, 50, 55, 60, 65, 70, 75, 80, 85, 90, 95, 100, or more than 100 years older than the second sample; or about 1, 2, 3, 4, 5, 6, 7, 8, 9, 10, 15, 20, 25, 30, 35, 40, 45, 50, 55, 60, 65, 70, 75, 80, 85, 90, 95, 100, or more than 100 years younger than the second sample.

The method may determine a likelihood of the biological age of the sample falling within the determined age range of the sample, such as at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

The method may determine biological age of the sample by classifying the sample into a determined categorical age among a set of two or more categorical ages (e.g., {"young" vs. "old"}, {"young" vs. "middle-aged" vs. "old"}). The set of two or more categorical ages may comprise about 2, about 3, about 4, about 5, about 6, about 7, about 8, about 9, about 10, or more than about 10 distinct categorical ages.

The method may determine a likelihood of the biological age of the sample falling within the determined categorical age of the sample, such as at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

The method may determine biological age of the sample with an accuracy (e.g., accuracy of classifying the sample into the determined categorical age among a set of two or more categorical ages) of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

The method may determine biological age of the sample with a sensitivity (e.g., sensitivity of classifying the sample into the determined categorical age among a set of two or more categorical ages) of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

The method may determine biological age of the sample with a specificity (e.g., specificity of classifying the sample into the determined categorical age among a set of two or more categorical ages) of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%. The method may determine biological age of the sample with a specificity (e.g., specificity of classifying the sample into the one categorical age among a set of two or more categorical ages) of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

The method may determine biological age of the sample with a positive predictive value (PPV) (e.g., PPV of classifying the sample into the determined categorical age among a set of two or more categorical ages) of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

The method may determine biological age of the sample with a negative predictive value (NPV) (e.g., NPV of classifying the sample into the determined categorical age among a set of two or more categorical ages) of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

The method may determine biological age of the sample with an Area Under Curve (AUC) of the Receiver Operator Characteristic (ROC) (e.g., AUC of classifying the sample into the determined categorical age among a set of two or more categorical ages) of at least about 0.50, at least about 0.55, at least about 0.60, at least about 0.65, at least about 0.70, at least about 0.75, at least about 0.80, at least about 0.85, at least about 0.90, at least about 0.95, at least about 0.96, at least about 0.97, at least about 0.98, or at least about 0.99.

The machine learning detection structure may comprise a neural network. The neural network may comprise a convolutional neural network (CNN). The convolutional neural network (CNN) may comprise a deep convolutional neural network (DCNN) (e.g., comprising multiple layers). The deep convolutional neural network (DCNN) may comprise a cascaded deep convolutional neural network. Alternatively, the CNN may comprise a simplified CNN or a shallow CNN (e.g., comprising one feature layer and/or one hidden layer). The biological age predictor may comprise a combination of deep learning architectures and/or other machine learning techniques, cascaded or chained together. For example, these cascades of machine learning architectures may be configured to generate intermediate results that are better processed by later parts in the chain or cascade, or to help interpret partial results coming from different parts of the chain or cascade. For example, deep learning architectures may comprise any combination of one or multiple convolutional neural networks (CNN), recurrent neural networks, and/or generative adversarial networks. In addition, machine learning techniques such as gradient boosting, random forests, and/or support vector machines may be incorporated into the biological age predictor. The biological age predictor may also be trained using training datasets using suitable methods appropriate for the one or more types of machine learning architectures used in the biological age predictor.

The computer program may include instructions, executable by the processor, to apply to the first sample data a network structure, such as a recurrent neural network structure or a general adversarial network structure. The results obtained from applying the machine learning detection structure may be combined with results obtained from applying the network structure to determine the biological age of the sample. The computer program may include instruction, executable by the processor, to apply to the first sample data a machine learning technique, such as gradient boosting, random forests, and support vector machines. The results obtained from applying the machine learning detection structure may be combined with results from applying the machine learning technique.

In some aspects, the present disclosure provides a computer-implemented method of determining the effectiveness of a substance by using a biological age predictor comprising: (a) providing data of a sample to said biological age predictor, wherein said biological age predictor identifies an aging factor; and (b) provide a substance to a subject based on said aging factor. In some embodiments, the computer-implemented method further comprises providing data of a second sample from said subject subsequent to providing said substance, wherein said biological age predictor applies machine learning to determine the biological age of said second sample. In an exemplary embodiment, the biological age predictor applies machine learning to identify an aging factor.

In another aspect, the present disclosure provides a computer-implemented method of identifying a druggable factor by using a biological age predictor. The method of identifying a druggable factor by using a biological age predictor may comprise providing data of a sample to the biological age predictor, generating a biological age from the biological age predictor, and identifying a druggable factor from the biological age predictor. The druggable factor may be a characteristic associated with aging, as described elsewhere herein. The method of identifying a druggable factor by using a biological age predictor may further comprise providing an active ingredient based on the identified druggable factor.

In another aspect, the present disclosure provides a computer-implemented method of determining the biological age of a sample using a biological age predictor. The method of determining the biological age of a sample using a biological age predictor may comprise providing data of a sample to the biological age predictor. The biological age predictor may generate a biological age. The method of determining the biological age of a sample using a biological age predictor may identify a feature without any input data by a user. In other words, the data of the sample provided to the biological age predictor may contain no user input to identify a feature.

In another aspect, the present disclosure provides a method of using a biological age predictor. The method of using a biological age predictor may comprise receiving initial data comprising a predicted biological age value from the biological age predictor. The method of using a biological age predictor may comprise automatically labeling the initial data with an extraction program, thereby producing labeled data. The extraction program may detect and uniquely label a desired feature with a first label. The method of using a biological age predictor may comprise processing the labeled data for use in a second biological age predictor. The second biological age predictor may be configured to determine the biological age of a sample subject based at least in part on identification of the desired feature.

Application to Drug Discovery

In another aspect, the present disclosure provides a method of using a biological age predictor for drug discovery. In some embodiments, the method is a computer-implemented method. The method of using a biological age predictor for drug discovery may comprise providing data of a sample to the biological age predictor. The biological age predictor may generate a first biological age for the sample. In some embodiments, the biological age predictor applies machine learning to generate a first biological age. After generating a first biological age for the sample, the method of using a biological age predictor for drug discovery may comprise treating the sample with an active ingredient, thereby generating a treated sample. After generating the treated sample, the method of using a biological age predictor for drug discovery may comprise providing data of the treated sample to the biological age predictor. The biological age predictor may generate a second biological age for the treated sample. In some embodiments, the biological age predictor applies machine learning to generate a second biological age.

In some embodiments, the sample is a cell sample. The cell sample may originate from primary cells or cell lines (e.g., grown cell cultures). The cell sample may comprise cells collected from or derived from one or more organs or tissues. For example, the cell sample may be a skin, fibroblast, muscle, blood, liver, heart, spleen, thymus, myobast, keratinocyte, and/or brain cell sample. In some embodiments, the sample is a tissue sample (e.g., a tissue cross-section). The tissue sample may comprise tissues collected from or derived from one or more organs or tissues. For example, the tissue sample may be a fibroblast, skin, muscle, blood, liver, myobast, keratinocyte, and/or brain tissue sample.

The biological age predictor may be a computer-implemented system which is trained to determine the biological age of the sample. The data provided to the biological age predictor may comprise an image, an epigenetic profile, a proteomic profile, or a metabolomics profile. The data may identify cell morphology, biomarkers, or cellular components. The substance to treat the sample, such as an active ingredient, may be a drug or potential drug, such as an anti-aging agent, a new drug entity, or an FDA approved drug entity. In some embodiments, the substance is a new drug entity. The active ingredient or candidates for the active ingredient may be identified or evaluated based on, for example, performing searches through tissue or cell samples, such as blood or plasma, for an aging factor or druggable targets (e.g., factors or proteins). For example, such aging factor or druggable targets or candidates for aging factors or druggable targets may be identified based on studies involving parabiosis, plasma injection, and/or blood transfusion. Examples of anti-aging compounds include oxytocin, TGFbeta, Wnt3a, Klotho, ALK5 inhibitor II, and PP242.

The method of using a biological age predictor for drug discovery may further comprise comparing the first biological age and the second biological age. By comparing the first biological age for the (untreated) sample and the second biological age for the treated sample, the effect of the active ingredient on the biological age of the sample may be assessed. For example, if the second biological age is less than the first biological age, then the effect of the active ingredient was to decrease the biological age of the sample. For example, if the second biological age is more than the first biological age, then the effect of the active ingredient was to increase the biological age of the sample. In some embodiments, the biological age of the second biological age is less than the first biological age.

The method of using a biological age predictor for drug discovery may determine the first biological age and the second biological age of the sample by determining a specific age of the sample, for example, about 1, 2, 3, 4, 5, 6, or 7 days; about 1, 2, 3, or 4 weeks; about 1, 2, 3, 4, 5, 6, 7, 8, 9, 10, 11, or 12 months; or about 1, 2, 3, 4, 5, 6, 7, 8, 9, 10, 15, 20, 25, 30, 35, 40, 45, 50, 55, 60, 65, 70, 75, 80, 85, 90, 95, 100, or more than 100 years. Determining the specific age of a sample may also include determining an expected mean error for the determined specific age, such as about 1, 2, 3, 4, 5, 6, or 7 days; about 1, 2, 3, or 4 weeks; about 1, 2, 3, 4, 5, 6, 7, 8, 9, 10, 11, or 12 months; or about 1, 2, 3, 4, 5, 6, 7, 8, 9, or 10 years. For example, the specific age of a sample may be determined with an expected mean error of no more than about 1, 2, 3, 4, 5, 6, 7, 8, 9, 10, 11, or 12 months; or no more than about 1, 2, 3, 4, 5, 6, 7, 8, 9, or 10 years. The method of using a biological age predictor for drug discovery may determine biological age of the sample by determining an age range of the sample, for example, between about 1-5 years, 5-10 years, 10-15 years, 15-20 years, 20-25 years, 25-30 years, 30-35 years, 35-40 years, 40-45 years, 45-50 years, 50-55 years, 55-60 years, 60-65 years, 65-70 years, 70-75 years, 75-80 years, 80-85 years, 85-90 years, 90-95 years, 95-100 years, 1-10 years, 10-20 years, 20-30 years, 30-40 years, 40-50 years, 50-60 years, 60-70 years, 70-80 years, 80-90 years, or 90-100 years. The method of using a biological age predictor for drug discovery may determine the first biological age and the second biological age of the sample by determining a relative age of the untreated sample in comparison to the treated sample, for example, about 1, 2, 3, 4, 5, 6, 7, 8, 9, 10, 15, 20, 25, 30, 35, 40, 45, 50, 55, 60, 65, 70, 75, 80, 85, 90, 95, 100, or more than 100 years older than the treated sample; or about 1, 2, 3, 4, 5, 6, 7, 8, 9, 10, 15, 20, 25, 30, 35, 40, 45, 50, 55, 60, 65, 70, 75, 80, 85, 90, 95, 100, or more than 100 years younger than the treated sample.

System for Biological Age Prediction

In another aspect, the present disclosure provides a computer-implemented system comprising: a digital processing device comprising: (a) a processor; (b) an operating system configured to perform executable instructions; (c) a memory; and (d) a computer program including instructions executable by the digital processing device to create an application applying machine learning detection structures to a plurality of sample data to determine the biological age of a sample. The application may comprise a software module applying a machine learning detection structure to the plurality of sample data. The detection structure may employ machine learning to screen locations in the sample to identify a feature, and classify the feature. The application may comprise a software module automatically generating a report. The report may contain information including the biological age of the sample from which the sample data was derived.

The machine learning detection structure may comprise a neural network. The neural network may comprise a convolutional neural network (CNN). The convolutional neural network (CNN) may comprise a deep convolutional neural network (DCNN) (e.g., comprising multiple layers). The deep convolutional neural network (DCNN) may comprise a cascaded deep convolutional neural network. Alternatively, the CNN may comprise a simplified CNN or a shallow CNN (e.g., comprising one feature layer and/or one hidden layer). In an exemplary embodiment, the methods described herein comprise DCNN.

The application of the system may run in real-time or near-real time, and generate a real-time or near real-time report containing information including the biological age of the sample. The plurality of sample data may be obtained by imaging, morphological profiling, cell painting, mass spectrometry, antibody chips, 2-F Fluorescence Difference Gel Electrophoresis (DIGE), mass spectrometric immunoassay (MSIA), or laser capture microdissection (LCM). The plurality of sample data may comprise image data.

The application of the system may further comprise a software module performing image preprocessing of the plurality of the sample data. The image preprocessing may include, for example, normalization, image enhancement, image correction, contrast enhancement, brightness enhancement, filtering with one or more filters, transformation, increasing image resolution, decreasing image resolution, increasing bit resolution, decreasing bit resolution, increasing image size, decreasing image size, increasing field-of-view, decreasing field-of-view, background subtraction, noise or artifact subtraction, image subtraction, lossy compression, or lossless compression. The normalization may include, for example, normalization of signal noise, sequencing reads, image channel balancing/combination, quality filtering, color balancing, color normalization, or a combination thereof. The normalization may include, for example, normalization of image format, image slice spacing, image intensity, image contrast, image saturation, image size, image orientation, or other image data properties of the image data. The plurality of sample data may be segmented into a plurality of 2D slices. The detection structure may employ the convolutional neural network (CNN) to screen locations in a portion of or each of the plurality of 2D slices of the segmented sample data. For example, the convolutional neural network (CNN) may use a sliding window methodology to identify the features and classify the features.

The convolutional neural network (CNN) may have 2 to 64 convolutional layers and 1 to 8 fully connected layers. For example, the convolutional neural network (CNN) may have 2, 4, 8, 16, 32, 64, or more convolutional layers and 1, 2, 3, 4, 5, 6, 7, 8, or more fully connected layers. The sliding window may have less than about 4,000 pixels by less than about 4,000 pixels, less than about 2,000 pixels by less than about 2,000 pixels, less than about 1,000 pixels by less than about 1,000 pixels, less than about 512 pixels by less than about 512 pixels, less than about 256 pixels by less than about 256 pixels, less than about 128 pixels by less than about 128 pixels, less than about 64 pixels by less than about 64 pixels, less than about 32 pixels by less than about 32 pixels, less than about 16 pixels by less than about 16 pixels, less than about 8 pixels by less than about 8 pixels, or less than about 4 pixels by less than about 4 pixels. For example, the sliding window may have a first dimension (e.g., along the x-axis) or less than 100, less than 500, less than 1,000, less than 2,000, less than 3,000, less than 4,000, or less than 5,000 pixels; and may have a second dimension (e.g., along the y-axis) or less than 100, less than 500, less than 1,000, less than 2,000, less than 3,000, less than 4,000, or less than 5,000 pixels. The convolutional neural network (CNN) may comprise a neural network instance selected randomly from a plurality of neural network instances. The second convolutional neural network (CNN) may comprise a neural network instance selected randomly from a plurality of neural network instances.

The application of the system may include a software module performing post-processing of one or a plurality of refined locations. For example, the post-processing may include characterizing centroid location, volume, shape, intensity, density, transparency, regularity, or a combination thereof.

The generated report may contain information about the sample data. For example, the generated report may contain an informational overlay on the sample data. As another example, the generated report may contain a sample data heat mapped to indicate confidence level. As another example, the generated report may contain a time course of a disease or growth and movement of a tumor over time. For example, the time course may be generated by applying the application to medical images captured at two or more time points to measure progression of the disease or growth and movement of the tumor over time.

The machine learning detection structure may be trained to identify disease related outcomes. For example, the machine learning detection structure may be trained to identify critical clinical signs of a disease. The machine learning detection structure may be trained using supervised learning and labeled training data, such as sample data labeled by a human expert and/or subjected to preprocessing for normalization.

The application of the system may determine a biological age of the sample by determining a specific age of the sample, for example, about 1, 2, 3, 4, 5, 6, or 7 days; about 1, 2, 3, or 4 weeks; about 1, 2, 3, 4, 5, 6, 7, 8, 9, 10, 11, or 12 months; or about 1, 2, 3, 4, 5, 6, 7, 8, 9, 10, 15, 20, 25, 30, 35, 40, 45, 50, 55, 60, 65, 70, 75, 80, 85, 90, 95, 100, or more than 100 years. The application of the system may determine biological age of the sample by determining an age range of the sample, for example, between about 1-5 years, 5-10 years, 10-15 years, 15-20 years, 20-25 years, 25-30 years, 30-35 years, 35-40 years, 40-45 years, 45-50 years, 50-55 years, 55-60 years, 60-65 years, 65-70 years, 70-75 years, 75-80 years, 80-85 years, 85-90 years, 90-95 years, 95-100 years, 1-10 years, 10-20 years, 20-30 years, 30-40 years, 40-50 years, 50-60 years, 60-70 years, 70-80 years, 80-90 years, or 90-100 years. The application of the system may determine biological age of the sample by determining a relative age of the sample in comparison to an additional sample, for example, about 1, 2, 3, 4, 5, 6, 7, 8, 9, 10, 15, 20, 25, 30, 35, 40, 45, 50, 55, 60, 65, 70, 75, 80, 85, 90, 95, 100, or more than 100 years older than the additional sample; or about 1, 2, 3, 4, 5, 6, 7, 8, 9, 10, 15, 20, 25, 30, 35, 40, 45, 50, 55, 60, 65, 70, 75, 80, 85, 90, 95, 100, or more than 100 years younger than the additional sample.

In another aspect, the present disclosure provides a non-transitory computer readable storage medium encoded with a computer program including instructions executable by a processor to create an application applying machine learning to a plurality of sample data to determine the biological age of a sample. The application may comprise a software module applying a machine learning detection structure to the plurality of sample data. The detection structure may employ machine learning to screen locations in the plurality of sample data to identify a feature and classify the feature. The application may comprise a software module automatically generating a report comprising the biological age of a sample from which the sample data was derived.

The machine learning detection structure may comprise a neural network. The neural network may comprise a convolutional neural network (CNN). The convolutional neural network (CNN) may comprise a deep convolutional neural network (DCNN) (e.g., comprising multiple layers). The deep convolutional neural network (DCNN) may comprise a cascaded deep convolutional neural network. Alternatively, the CNN may comprise a simplified CNN or a shallow CNN (e.g., comprising one feature layer and/or one hidden layer). In an exemplary embodiment, the methods disclosed herein comprise DCNN.

Computer Systems

Figure 4:
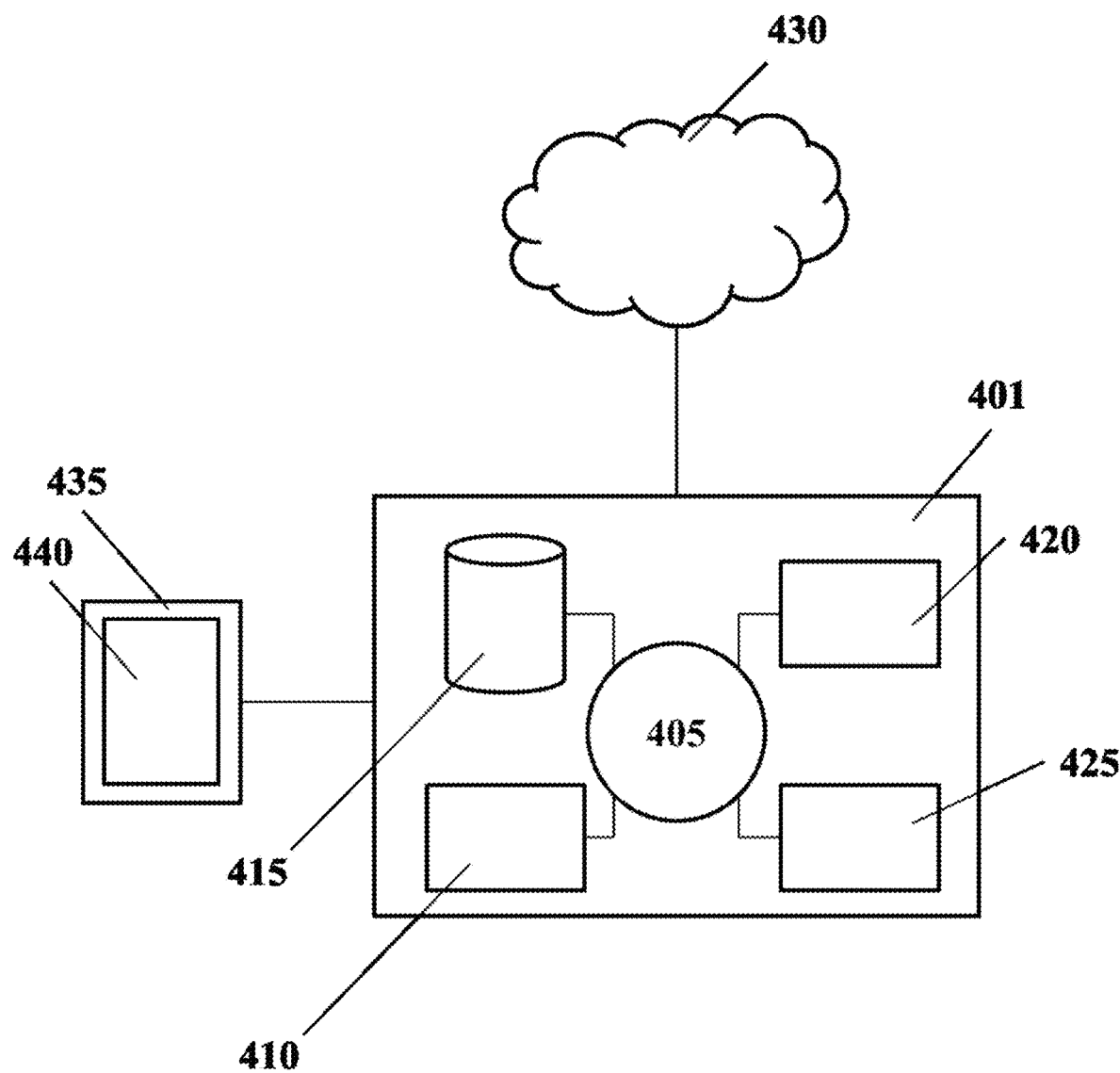
FIG. 4 illustrates a computer control system that is programmed or otherwise configured to implement methods provided herein.

The present disclosure provides computer systems that are programmed to implement methods of the disclosure. FIG. 4 shows a computer system 401 that is programmed or otherwise configured to: apply a machine learning detection structure to sample data, employ machine learning to screen locations in sample data, identify features, classify features to labels, or determine biological ages of subjects based at least in part on the identified and classified features.

The computer system 401 can regulate various aspects of methods and systems of the present disclosure, such as, for example, applying a machine learning detection structure to sample data, employing machine learning to screen locations in sample data, identifying features, classifying features to labels, and determining biological ages of subjects based at least in part on the identified and classified features.

The computer system 401 can be an electronic device of a user or a computer system that is remotely located with respect to the electronic device. The electronic device can be a mobile electronic device. The computer system 401 includes a central processing unit (CPU, also "processor" and "computer processor" herein) 405, which can be a single core or multi core processor, or a plurality of processors for parallel processing. The computer system 401 also includes memory or memory location 410 (e.g., random-access memory, read-only memory, flash memory), electronic storage unit 415 (e.g., hard disk), communication interface 420 (e.g., network adapter) for communicating with one or more other systems, and peripheral devices 425, such as cache, other memory, data storage and/or electronic display adapters. The memory 410, storage unit 415, interface 420 and peripheral devices 425 are in communication with the CPU 405 through a communication bus (solid lines), such as a motherboard. The storage unit 415 can be a data storage unit (or data repository) for storing data. The computer system 401 can be operatively coupled to a computer network ("network") 430 with the aid of the communication interface 420. The network 430 can be the Internet, an internet and/or extranet, or an intranet and/or extranet that is in communication with the Internet. The network 430 in some cases is a telecommunication and/or data network. The network 430 can include one or more computer servers, which can enable distributed computing, such as cloud computing. The network 430, in some cases with the aid of the computer system 401, can implement a peer-to-peer network, which may enable devices coupled to the computer system 401 to behave as a client or a server.

The CPU 405 can execute a sequence of machine-readable instructions, which can be embodied in a program or software. The instructions may be stored in a memory location, such as the memory 410. The instructions can be directed to the CPU 405, which can subsequently program or otherwise configure the CPU 405 to implement methods of the present disclosure. Examples of operations performed by the CPU 405 can include fetch, decode, execute, and writeback.

The CPU 405 can be part of a circuit, such as an integrated circuit. One or more other components of the system 401 can be included in the circuit. In some cases, the circuit is an application specific integrated circuit (ASIC).

The storage unit 415 can store files, such as drivers, libraries and saved programs. The storage unit 415 can store user data, e.g., user preferences and user programs. The computer system 401 in some cases can include one or more additional data storage units that are external to the computer system 401, such as located on a remote server that is in communication with the computer system 401 through an intranet or the Internet.

The computer system 401 can communicate with one or more remote computer systems through the network 430. For instance, the computer system 401 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 401 via the network 430.

Methods as described herein can be implemented by way of machine (e.g., computer processor) executable code stored on an electronic storage location of the computer system 401, such as, for example, on the memory 410 or electronic storage unit 415. The machine executable or machine readable code can be provided in the form of software. During use, the code can be executed by the processor 405. In some cases, the code can be retrieved from the storage unit 415 and stored on the memory 410 for ready access by the processor 405. In some situations, the electronic storage unit 415 can be precluded, and machine-executable instructions are stored on memory 410.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 401 can include or be in communication with an electronic display 435 that comprises a user interface (UI) 440 for providing, for example, user selection of algorithms, binding measurement data, candidate proteins, and databases. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 405. The algorithm can, for example, apply a machine learning detection structure to sample data, employ machine learning to screen locations in sample data, identify features, classify features to labels, or determine biological ages of subjects based at least in part on the identified and classified features.

EXAMPLES

Example 1

Biological Age Prediction by Analysis of Human Skin Tissue

Biological age prediction was performed by analysis of human skin tissue. Skin samples were collected from a set of 105 healthy human donors in three different age ranges: 35 donors in a 'young' age group (18-35 years old, denoted by "Y"), 35 donors in a 'middle-aged' age group (42-50 years, denoted by "M"), and 35 donors in an 'old' age group (65-80, denoted by "O"). The set of 105 healthy human donors included an uneven mix of female and male subjects (89% female subjects and 11% male subjects). Skin samples were obtained from subjects at bodily locations with reduced sun exposure (e.g., breast, abdomen, and other less exposed areas). No foreskin was obtained for the skin samples. Donors having a disease or disorder (e.g., severe obesity, acute illness such as cancer, or chronic illness such as diabetes) were excluded from the study. Samples are typically obtained from healthy subjects during aesthetic surgeries, such as abdomen reduction or breast surgery. Only skin phototypes 2 and 3 are included, as defined by the Fitzpatrick skin phototype scale (described by, for example, D'Orazio et al., "UV Radiation and the Skin," *Int. J. Mol. Sci.* 2013, 14(6), 12222-12248, 7 Jun. 2013, which is hereby incorporated by reference in its entirety).

Next, tissue samples and slides were prepared as follows. Sample acquisition and frozen tissue block preparation were performed by a partner hospital. Specimens were obtained directly from patients during surgery and were frozen down into blocks. The frozen tissue specimens were then sliced with a cryotome at a thickness of 5 microns and placed onto glass slides. At least 3 slides were acquired from each donor, each slide including at least two pieces of tissue from the donor.

Next, three different immunohistochemistry stains were performed on each donor's sample by staining each individual slide with one of three histological stains: (1) HES (hematoxylin eosin saffron) stain, (2) Luna stain, and (3) Herovici stain, while ensuring that at least one of each donor's slides is stained with all three immunohistochemistry stains. Since the process of staining slides may be able to stain only 20 slides at a time, slides were batched into groups of 20 during staining, while ensuring that each batch of slides contained equal representation across all three donor age groups.

Next, images were acquired as follows. High-resolution full-slide digital images were acquired for all slides using a high-throughput slide scanner. Images were acquired at a magnification of 40× and a resolution of 0.5 microns per pixel. Alternatively, images can be acquired at a magnification of about 2×, 5×, 10×, 20×, 60×, 80×, 100×, 200×, 400×, 600×, 800×, 1000×, or 1500×, and at a resolution of about 1.4, about 1.0, about 0.5, about 0.25, about 0.2, about 0.1, about 0.08, about 0.075, about 0.06, about 0.05, about 0.04, about 0.025, about 0.02, or about 0.01 microns per pixel. The slides were scanned in brightfield.

Next, the data were prepared as follows. To analyze the biological age of the acquired images, the large high-resolution whole-slide images were first tiled into many smaller square image tiles of 128-, 256-, and 512-pixel sizes using a sliding tiling window. This dataset of at least about 6,500 (depending on the pixel sizes chosen) image tiles were partitioned into training and test sets with proportions of ⅔ and ⅓, respectively. The selection was done randomly, but such that any given donor has all of his or her image tiles belonging to either the training set or the test set. Further, all three different partitions or "folds" of the data were tested. Analyses were performed as described below, and the average performance across all three folds is reported, unless otherwise specified.

Next, the data was analyzed using a machine learning analysis approach as follows. Analyses of the acquired images were performed by first training a deep convolutional neural network. During the training process, images were sampled randomly from the training set using mini-batches of 32 images at a time and inputted to the neural network along with labels representing their true ages. The neural network is configured to calculate a set of predictions for each image, and a ranked probability loss is computed which is indicative of a comparison between the predicted and the true age. A standard gradient descent algorithm using an "Adam" optimizer (described by, for example, Kingma et al., "Adam: A Method for Stochastic Optimization," arXiv.org, 30 Jan. 2017, which is hereby incorporated by reference in its entirety) (with a learning rate of 0.0001, a beta1 value of 0.9, and a beta2 value of −0.999) was then applied to adjust a set of parameters (e.g., weights) of the neural network in response to this loss so as to improve its predictive abilities as more training images are fed in. A single pass through the entire training set was considered a single epoch, and training proceeded until the ranked probability loss of the entire validation set does not improve over 4 consecutive epochs.

The deep convolutional network architecture used may be referred to as "ResNet-50", and employs a very deep neural network composed of several "residual blocks" (described by, for example, He et al., "Deep Residual Learning for Image Recognition," arXiv.org, 10 Dec. 2015, which is hereby incorporated by reference in its entirety). Because training these large networks often presents challenges, in the training process, the network was first initialized using weights that were optimized for general object recognition on the ImageNet dataset (described by, for example, Deng et al., "ImageNet: A Large-Scale Hierarchical Image Database," *Conference on Computer Vision and Pattern Recognition*, 2009, which is hereby incorporated by reference in its entirety). The first four residual blocks were frozen such that their weights cannot change, and the fifth and final block was unfrozen so as to be able to be updated in the training process described above. Further, the ResNet architecture was extended with an additional fully-connected layer that has the same number of outputs as there are classes in the classification structure. That final layer is passed through a softmax activation layer, so as to make the final prediction a probability vector among the classes.

Finally, because the model has significant capacity to learn extremely complex functions, the training process artificially introduces noise to the training set to help the neural network improve the generalization of its predictive abilities. Notably, each time an image is sampled from the training set, a series of transformation operations were applied at random: a horizontal flip with a probability of 50%, a vertical flip with a probability of 50%, a rotation of 90 degrees with a probability of 25%, a rotation of 180 degrees with a probability of 25%, and a rotation of 270 degrees with a probability of 25%.

The biological age predictions were produced using a classification system (e.g., predicting age groups) instead of a regression analysis (e.g., predicting numeric age). A classification system was selected because the data has a large number of donors in a small number of discrete classes, which makes classification a more suitable study than regression.

Biological age predictions were validated using the test sets described above in two different manners: prediction of age group of individual image tiles and prediction of age group of donors (by aggregating tile predictions). The final predicted age of a tile was taken as the age group the model assessed with the highest likelihood. The final predicted age of a donor was taken as the certainty-weighted average of all age predictions of its constituent tiles.

Figure 5A:
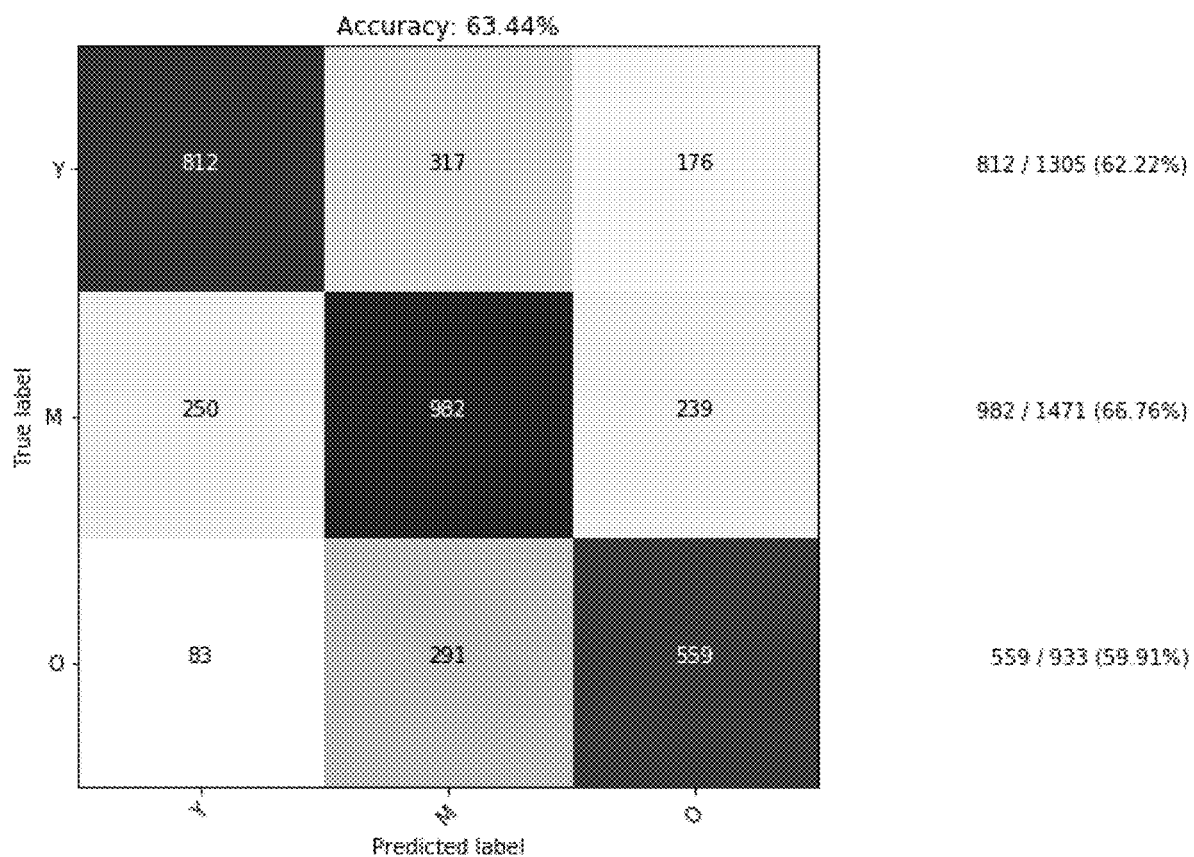
FIG. 5A illustrates an un-aggregated per-tile confusion matrix for an example fold of a biological age prediction by analysis of human skin tissue.
Figure 5B:
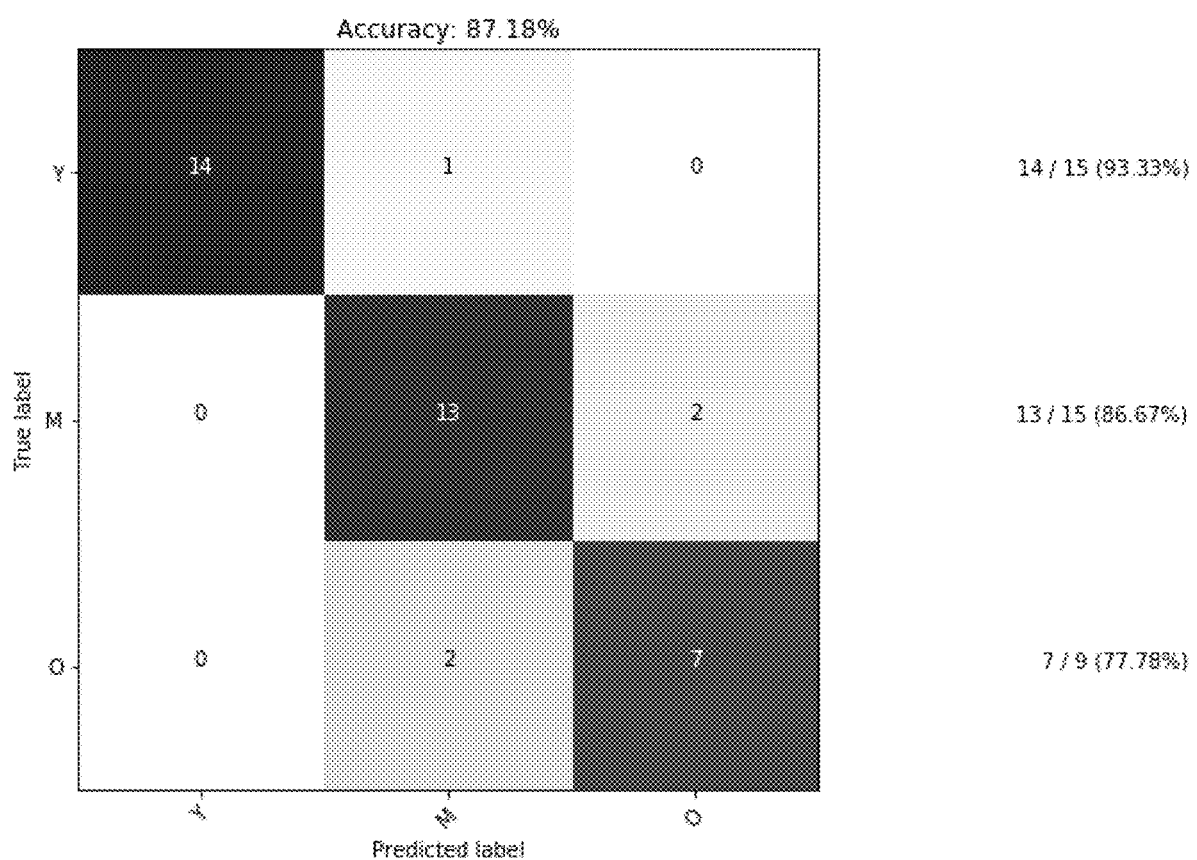
FIG. 5B illustrates a donor-aggregated confusion matrix for an example fold.
Figure 5C:
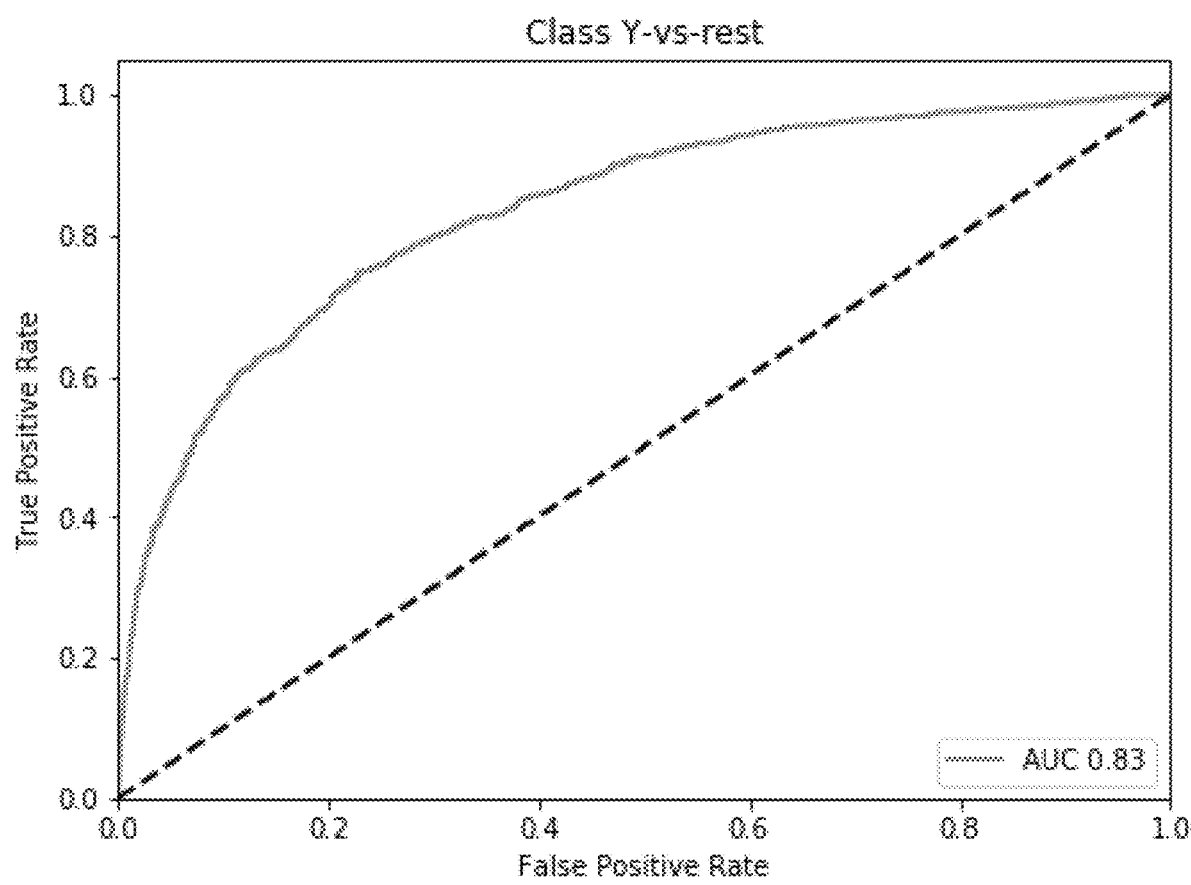
FIGS. 5C-5E illustrate un-aggregated "1-vs.-rest" per-tile ROC (receiver-operating characteristic) curves indicating each age group's "1 vs rest" classification performance, which represents the likelihood of correctly predicting one correct age group versus all other incorrect age groups combined ("Class Y-vs.-rest", "Class M-vs.-rest", and "Class O-vs.-rest" per-tile ROC curves for Y vs. M vs. O classification, respectively).
Figure 5D:
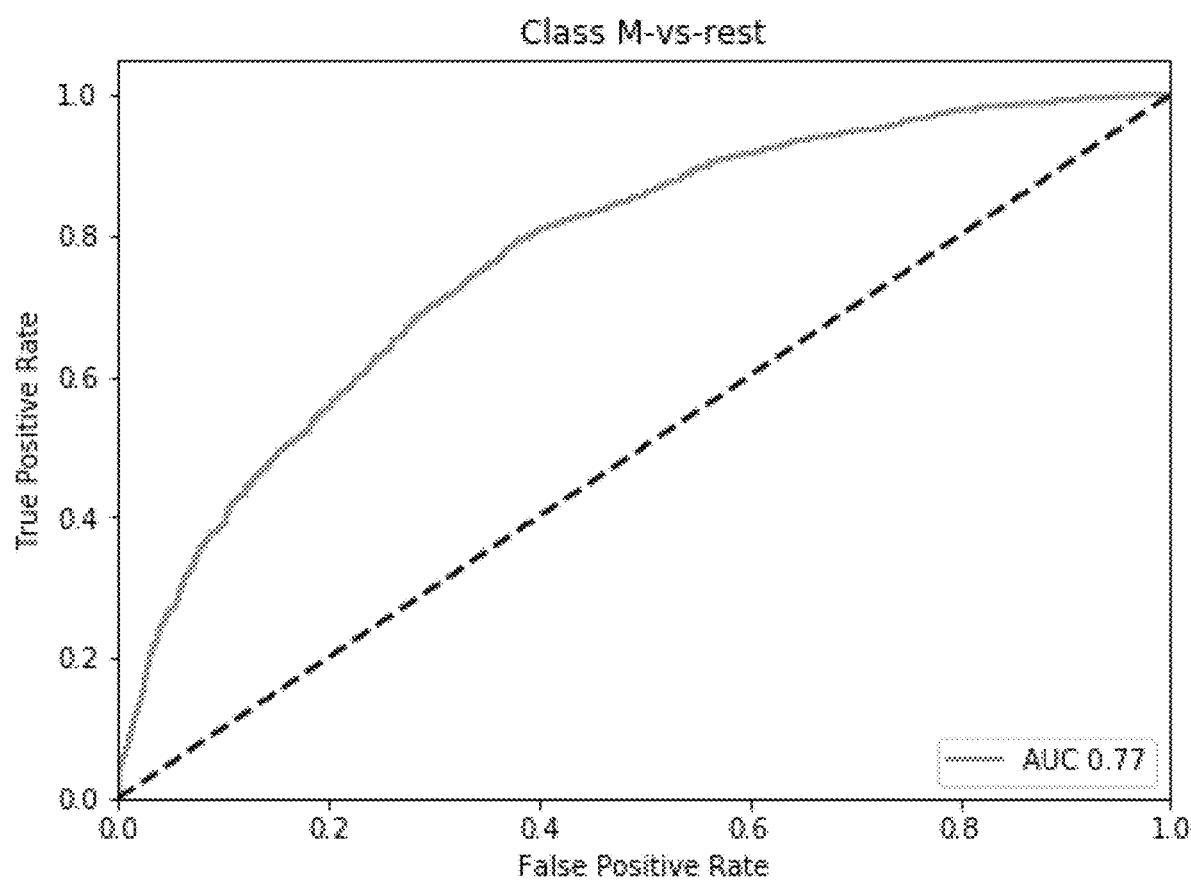
Figure 5E:
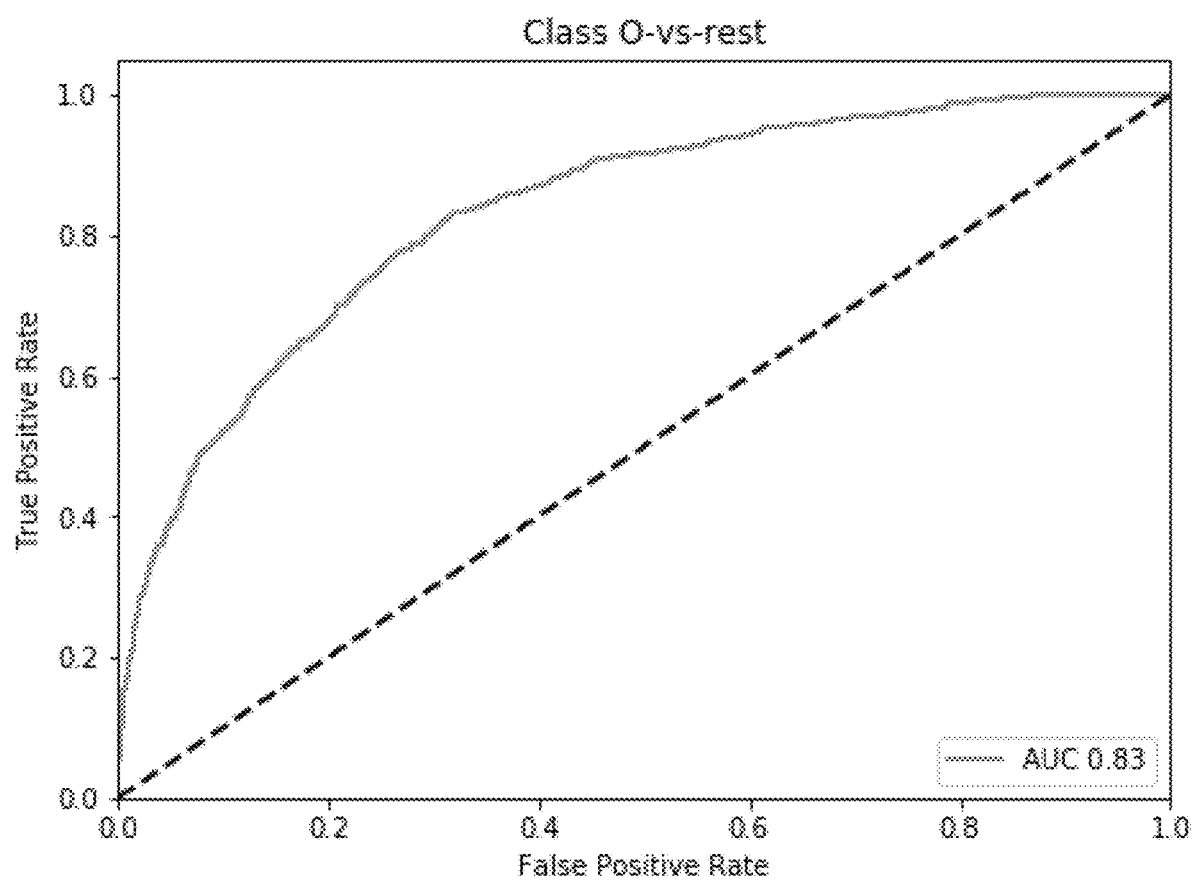
Figure 6A:
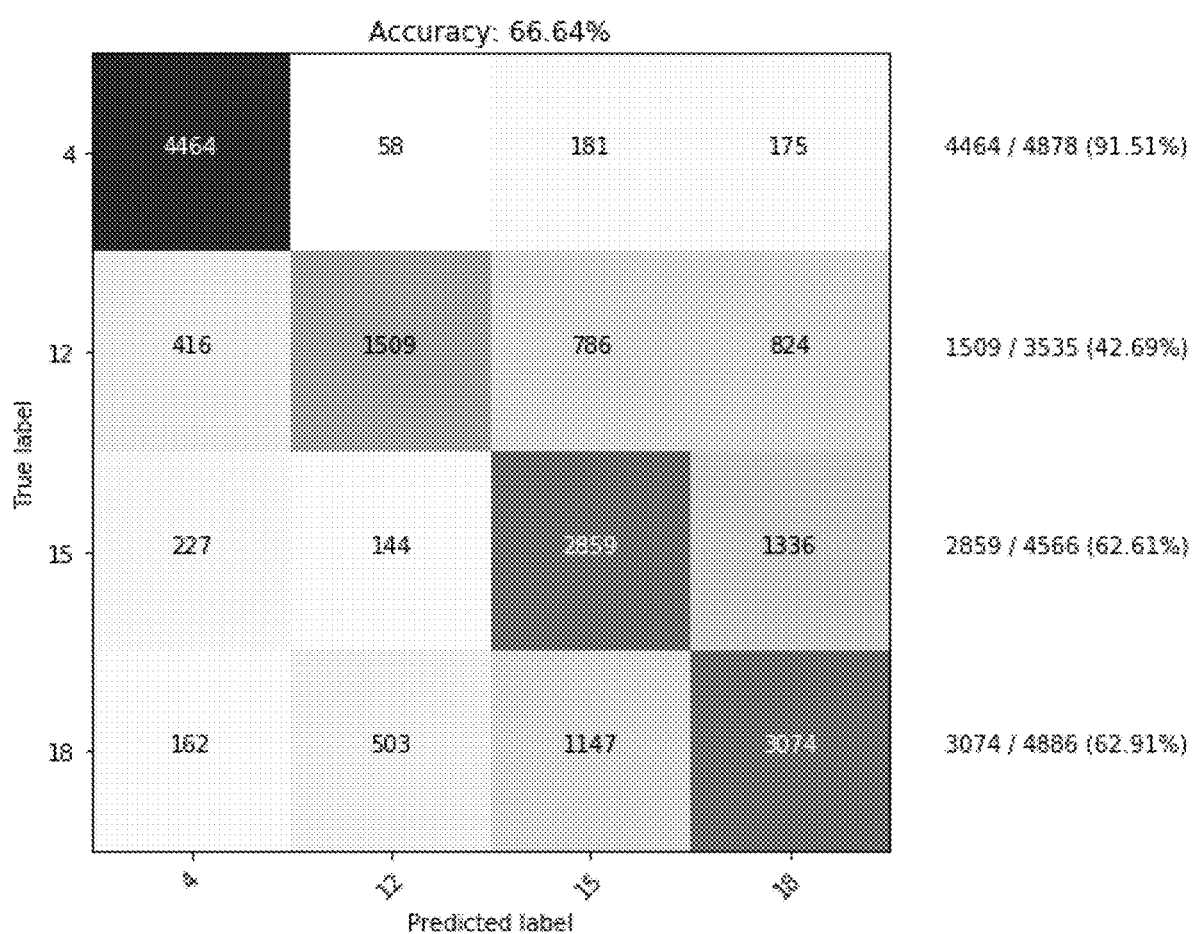
FIG. 6A illustrates an un-aggregated per-tile confusion matrix for an example fold of a biological age prediction by analysis of mouse skin tissue.
Figure 6B:
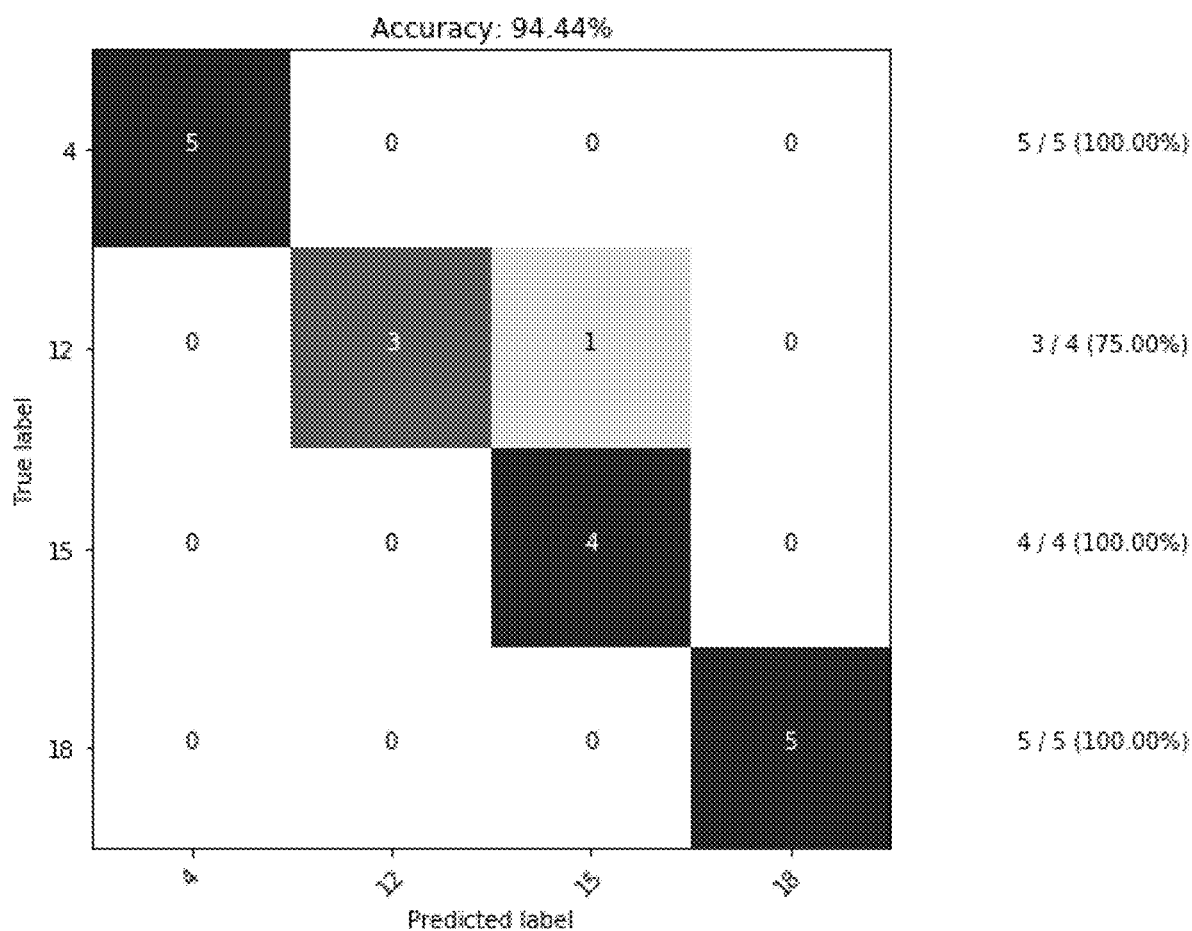
FIG. 6B illustrates a donor-aggregated confusion matrix for an example fold.
Figure 6C:
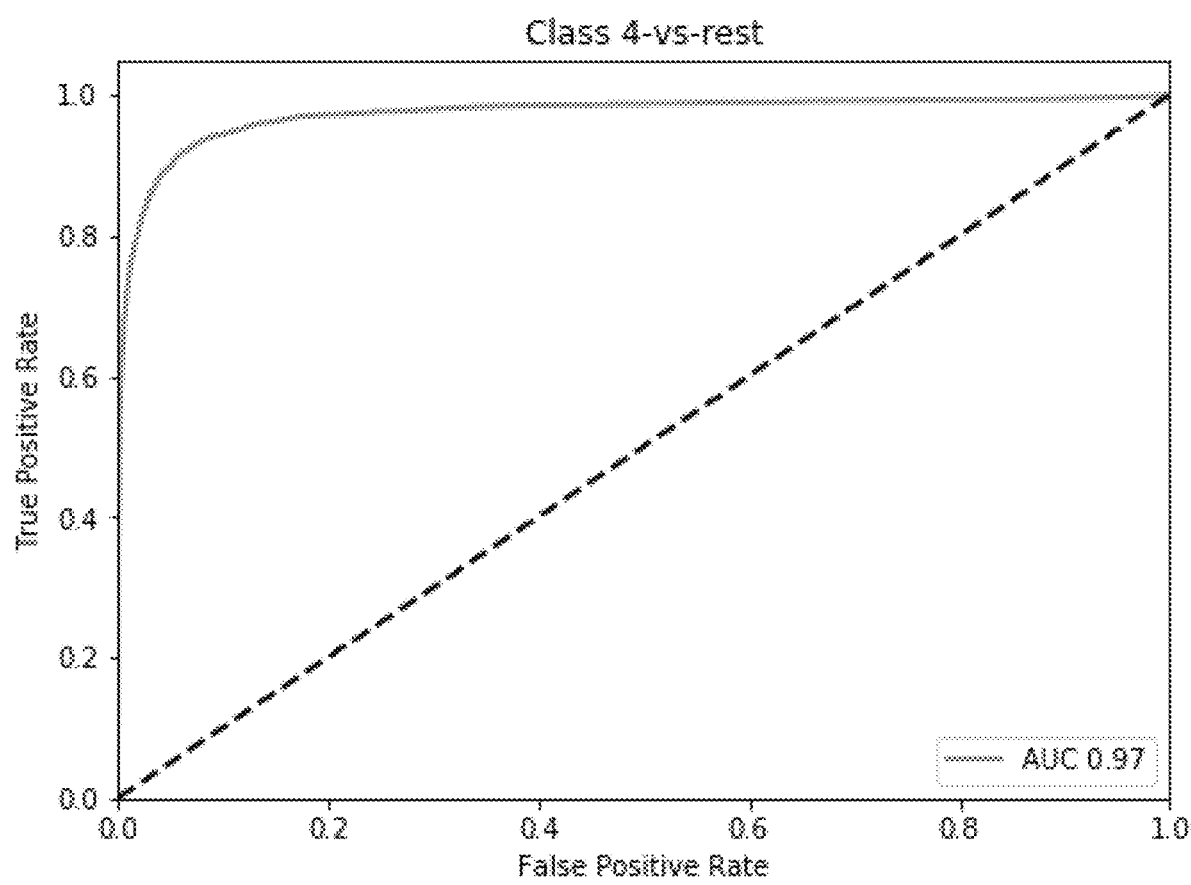
FIGS. 6C-6F illustrate un-aggregated "Class 4-vs.-rest", "Class 12-vs.-rest", "Class 15-vs.-rest", and "Class 18-vs.-rest" per-tile ROC curves for 4 vs. 12 vs. 15 vs. 18 classification, respectively.
Figure 6D:
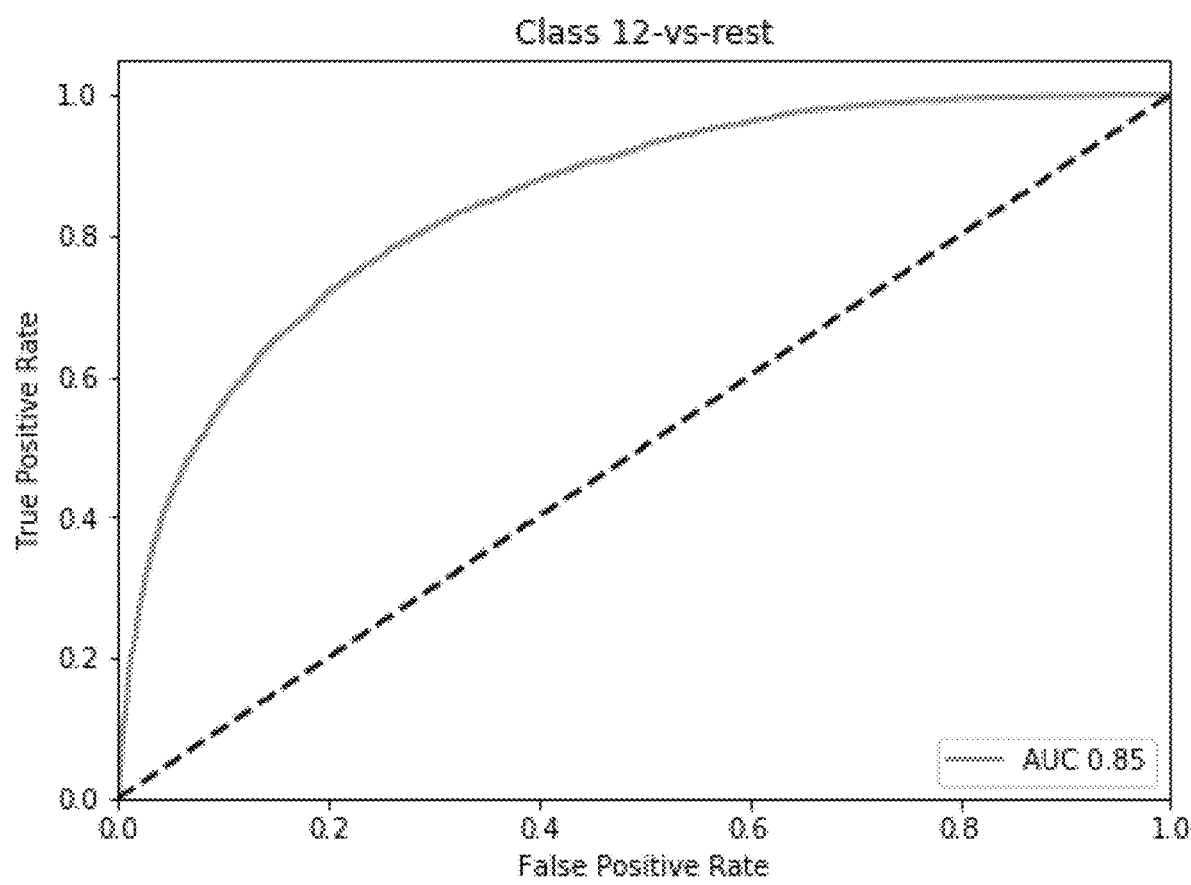
Figure 6E:
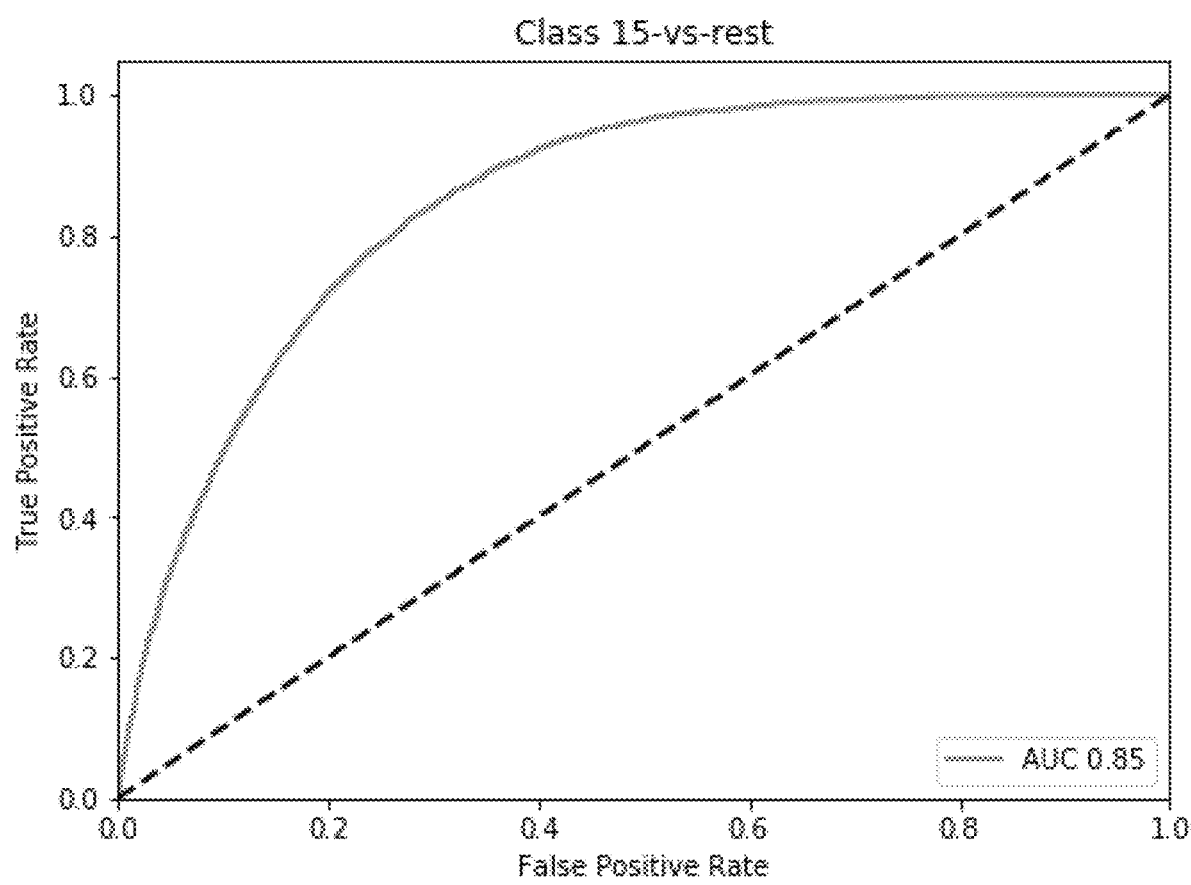
Figure 6F:
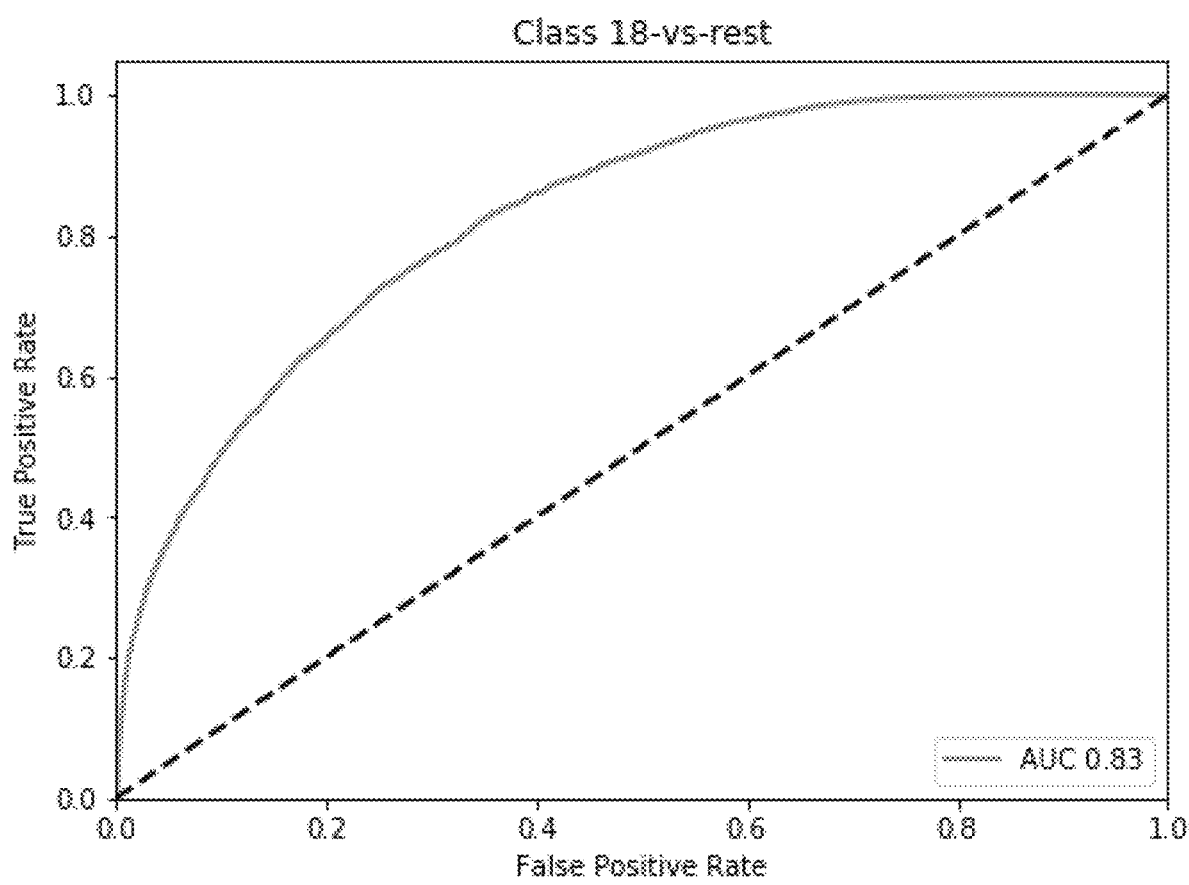

The results are illustrated in FIGS. 5A-5E using two approaches. First, confusion matrices are shown for all tiles (FIG. 5A, an un-aggregated per-tile confusion matrix for an example fold) and for donors (FIG. 5B, a donor-aggregated confusion matrix) in the validation set. These confusion matrices illustrate which age groups were predicted correctly, which were predicted incorrectly, and where the most frequent mistakes were made. Second, FIGS. 5C-5E illustrate un-aggregated "1-vs.-rest" per-tile ROC (receiver-operating characteristic) curves indicating each age group's "1 vs rest" classification performance, which represents the likelihood of correctly predicting one correct age group versus all other incorrect age groups combined ("Class Y-vs.-rest", "Class M-vs.-rest", and "Class O-vs.-rest" per-tile ROC curves for Y vs. M vs. O classification, respectively). In particular, AUC (Area Under the Curve) values of 0.83, 0.77, and 0.83 were achieved for the "Class Y-vs.-rest", "Class M-vs.-rest", and "Class O-vs.-rest" classifications, respectively.

Using the above assessments, the biological age of human skin tissue samples were predicted with excellent accuracy for both individual tile and donor predictions, as shown in Table 1.

TABLE 1

Accuracy of biological age prediction of human skin tissue samples

| Classification type | Tile prediction accuracy | Donor prediction accuracy |
| --- | --- | --- |
| Y vs. M vs. O | 65% | 86% |
| Y vs. O | 76% | 87% |

Example 2

Biological Age Prediction by Analysis of Mouse Skin Tissue

Biological age prediction was performed by analysis of mouse skin tissue. Skin samples were collected from a set of 50 healthy C57BL/6J mice from four separate age groups: 15 mice are 4 months old (denoted by "4"), 10 mice are 12 months old (denoted by "12"), 10 mice are 15 months old (denoted by "15"), and 15 mice are 18 months old (denoted by "18"). Both dorsal and ventral skin samples were collected from each mouse. C57BL/6J mice are typically considered "old" when they reach 18 months old, which roughly correlates to about a 56 to 69-year-old human. At this age, this type of mouse shows senescent changes, and at 24+ months ("very old"), survivorship drops off rapidly (as described by, for example, Jackson Labs and Flurkey et al., "The mouse in biomedical research" in James G. Fox (ed.), American College of Laboratory Animal Medicine series, 2007, which is hereby incorporated by reference in its entirety).

At termination, the mice were perfused with normal buffer formalin 10%. Skin samples were obtained and then fixed for 24 to 48 hours after collection in the same buffer, and the samples were shipped in 70% ethanol.

Next, tissue samples and slides were prepared as follows. Tissues were shipped from a partner lab, which performed sample collection as described in Example 1, to another partner lab that produced paraffin blocks and slides from the samples.

Tissue samples were prepared in a specific way in order to reduce processing and batching effects on subsequent aging analysis. Each tissue sample was cut into 6 pieces of 5 mm each, and each piece was embedded in an independent paraffin block. This process produced 12 independent paraffin blocks per mouse, 6 from dorsal skin and 6 from ventral skin. Each block was sectioned into slides at a thickness of 5 microns. Each slide contained 6 separate sections of tissues from the same paraffin block, producing a total of 600 slides.

Next, the slides were stained using HES (hematoxylin eosin saffron) stain. Since the process of staining slides may be able to stain only 20 slides at a time, slides were batched into groups of 20, while ensuring that each batch of slides contained balanced representation of slides across two dimensions of the data: each of the four age groups is represented in each batch at a rate proportional to their presence in the entire dataset (for example, the oldest and youngest groups have more slides in each batch than the middle two groups), and each batch has equal representation of both ventral and dorsal skin samples. This deliberate batching process was performed in order to minimize biases that may be introduced by the per-batch staining process.

Next, images were acquired as follows. Full-resolution digital slide images were acquired for all slides using a high-throughput slide scanner. Images were acquired at a magnification of 40× and a resolution of 0.25 microns per pixel. The slides were scanned in brightfield.

Next, the data were prepared using a similar process as that described in Example 1. The slides were segmented into smaller square tiles, and each of the mice's data were partitioned into training and test sets with proportions of ⅔ and ⅓, respectively, while ensuring that no mouse has data appearing in both the training and test sets at the same time. This resulted in a full dataset of more than about 55,000 images. Analyses were performed as described below, and the average performance across three different training and test folds are reported, unless otherwise specified.

Next, the data was analyzed using a similar deep convolutional neural network architecture and the machine learning analysis approach described in Example 1. The final network layer is changed so that the number of outputs corresponds to the number of classes in the problem structure, but all other hyper-parameters of the approach are unchanged.

As discussed in Example 1, the biological age predictions were produced using a classification system (e.g., predicting age groups) in two different manners (using both tile and donor predictions). The results are illustrated in FIGS. 6A-6F using confusion matrices (FIGS. 6A-6B, un-aggregated per-tile and donor-aggregated confusion matrices for "4 vs. 12 vs. 15 vs. 18" classification) and ROC plots (FIGS. 6C-6F, un-aggregated "Class 4-vs.-rest", "Class 12-vs.-rest", "Class 15-vs.-rest", and "Class 18-vs.-rest" per-tile ROC curves for 4 vs. 12 vs. 15 vs. 18 classification, respectively), as described in Example 1. In particular, AUC values of 0.97, 0.85, 0.85, and 0.83 were achieved for the "Class 4-vs.-rest", "Class 12-vs.-rest", "Class 15-vs.-rest", and "Class 18-vs.-rest" classifications, respectively.

The results for biological age prediction by analysis of mouse skin tissue show that biological age of mouse skin tissue is predicted with excellent accuracy for both individual tile and mouse predictions, as shown in Table 2. These results for mouse skin tissue shows even higher performance than that for human skin tissue. This observation may be expected, since all below mice are from the same genetic background and raised identically. The results for human skin tissue reported in Example 1 are encouraging due to the natural biological variability of humans. This heterogeneity is exacerbated with age. Further, success is reported predicting the biological age of 4-18 month old mice. The machine learning approach may produce even greater accuracy when used to analyze mouse samples of age closer to 24 months.

TABLE 2

Accuracy of biological age prediction of mouse skin tissue samples

| Classification type | Tile prediction accuracy | Mouse prediction accuracy |
|---|---|---|
| 4 vs. 12 vs. 15 vs. 18 | 66.4% | 94.0% |
| 4 vs. 18 | 92.4% | 100% |

Example 3

Biological Age Prediction by Analysis of Mouse Myoblast Cells

Biological age prediction was performed by analysis of mouse myoblast cells.

Cell samples were acquired and prepared as follows. To build a cell bank for analyses disclosed herein, skeletal muscle myoblasts were isolated from 52 healthy male C57BL/6J mice in two different age ranges: 20 mice were 4 months old ("young" or "Y") and 32 mice were 18 months old ("old" or "O").

Before isolation of the cells, in order to increase the number of myoblasts isolated, a muscle injury model was used which included degeneration of muscle fiber by cardiotoxin: Naja mossambica venom. Under anesthesia, two injections of 5 mL each were performed in the tibialis anterior in the hind leg of each mouse at a concentration of 0.2 mg/mL. Four injections of 10 mL each was also performed in the gastrocnemius at the same concentration. A 28-gauge needle was used, and all injections were performed at the same time.

After a sufficient time (about 3 days) to allow the cells to activate and divide but not enough time to fuse into myotubes, the mice were euthanized, and both the tibialis anterior and gastrocnemius of the mice were dissected. The muscle tissues were then incubated in Collagenase type II (250 U/mL) at 37° C. for 1.5 hours for enzymatic digestion. The muscle was then washed in PBS (phosphate-buffered saline) and mechanically disrupted by triturating and pipetting up and down with a broken end glass Pasteur pipette, thereby dissociating the tissue into muscle fibers.

Next, a second digestion of the muscle fibers was performed to release the cells from the fiber. This digestion was performed using Collagenase type II (40 U/mL)/Dispase (2 U/mL) at 37° C. for 1 hour. After 2 rounds of washing and centrifugation, the cells were resuspended in 10-20 mL of Ham's F10 supplemented with 10% horse serum. Cells were then pre-plated onto non-coated tissue culture dishes. This step of pre-plating was used to reduce the number of fibroblasts and to enrich myoblasts. After 30 minutes, the cell suspension was collected, the cells were centrifuged, and the cells are resuspended in Ham's F10 basal medium with 20% BGS (bovine growth serum) and 5 ng/mL of basic FBF (fibroblast growth factor). Next, the cells were plated onto matrigel-coated dishes. Finally, the cells were cultured for 2 days, fed every day with the previous media, and then frozen down in cryostor cs10 media.

Because all the mice cannot be isolated at once, 6 separate isolation runs were performed as described above, and each isolation run always included a representative split of young and old mice. This process generated 52 different primary myoblast lines at passage 1 to be used below.

Next, images were acquired as follows for testing biological age prediction. A set of 12 young primary myoblast lines and 12 old primary myoblast lines were individually cultured, stained, and imaged. All 24 primary myoblasts (12 young and 12 old) were thawed on matrigel coated dishes at a density of 20,000 cells/cm$^2$ in myoblast growth media (Ham's F10 basal medium with 20% BGS (bovine growth serum) and 5 ng/mL of basic FGF (fibroblast growth factor)). The cells were fed daily due to the FGF's heat liability (causing rapid degradation). After 48 hours, the cells were lifted from the plate using DPBS (Dulbecco Phosphate Buffer Saline) without $Ca^{2+}$, $Mg^{2+}$.

The cells were seeded in 384-well matrigel-coated plates at around 3,000 cells per well. Particular attention was made at each step to ensure that any experimenter working with the cells handled both young and old cells at the same time. Again, this step is taken to minimize any experimental bias introduced between young and old samples. The plate layout was also specifically designed to minimize experimental bias caused by the well position in the plate (as described in the plate layout section of, for example, Bray et al., "Cell Painting, a high-content image-based assay for morphological profiling using multiplexed fluorescent dyes," Nat. Protoc., 25 Aug. 2016, which is hereby incorporated by reference in its entirety). In addition, only 240 wells are used in the 384-well plate layout in order to limit edge effects from the wells on the edge of the plate. Each of the 24 primary myoblast lines were plated in 10 replicate wells, covering all 240 used wells.

After plating (e.g., at 24 hours post-plating), the cells were fed with myoblast growth media. At 48 hours post-plating, the cells were stained for Cytopainter ER Green, Desmin antibody, Click IT EdU 647, and counterstain for Hoechst. As a first step, before the cells are fixed, the cells were labeled with EdU (5 uM EdU for 30 minutes according to manufacturer's instructions: Invitrogen catalog #C10356). The cells were fixed with 4% PFA in PBS for 20 minutes at room temperature, then permeabilized in a mixture of PBS and 0.3% Triton X-100. The cells were then blocked using Goat Block Buffer at 4° C. overnight. The cells were then incubated in Rabbit-anti-Desmin antibody at 1:200 dilution in Goat Block Buffer at 4° C. overnight. The cells were then incubated in secondary antibodies and dye for one hour at room temperature using a label mix comprising Cytopainter ER Green (1:1000 dilution), Hoechst, and AlexaFluor 568 Gt-a-Rb (1:500 dilution). The plates were sealed in preparation for imaging.

A high-throughput automated imager was used to capture 25 non-overlapping fields per well at a magnification of 40× with a separate image captured for each of the 4 stain channels plus brightfield. This image acquisition produced about 30,000 unique non-overlapping field images (2208 pixels wide) per plate (5 channels×240 wells×25 fields per well).

Next, the data were prepared using a similar process as that described in Examples 1 and 2. The cellular image datasets were partitioned into training and test sets with proportions of ⅔ and ⅓, respectively, while ensuring that no mouse has data appearing in both the training and test sets at the same time and that the splits are done in equal proportion among the two age groups. Analyses were performed as described below, and the average performance across three different training and test folds are reported, unless otherwise specified.

For the analyses below, all combinations of the microscopy cell stains used were tested, and the stain combination identified as being the most predictive of biological age was chosen.

The high-resolution images were also transformed using a standard normalization approach. First, the mean and the standard deviation of the intensity of each image channel was calculated across the entire dataset. Each image then had its intensity transformed by subtracting the mean intensity for the whole dataset from each image channel, then having the intensity value divided by the whole dataset's standard deviation. This created a "zero-mean, unit-variance" dataset across all of the images.

Next, the data was analyzed using a similar deep convolutional neural network architecture and the machine learning analysis approach described in Examples 1 and 2. Again, the output layer was altered so that the number of output layers corresponds to the number of classes in the problem structure, which in this case is two.

A single epoch of training for cellular images comprised iterating through all images once. However, because the images are high-resolution and large, they were first downsampled to half the resolution (1104 pixels wide) and a random 512-pixel square crop was first sampled within that field before inputting into the neural network. Hence, only a subset of the data was trained on in a given epoch, but that subset varies with each epoch.

Duplicate experiments were performed as follows. The above procedure to process the 24 primary myoblast lines was performed twice (including acquiring images, preparing and transforming the data, and analyzing the data using a deep convolutional neural network architecture and the machine learning analysis approach disclosed herein, using two separate collections of 24 primary myoblast lines taken from the original bank of 52 produced as described above. These duplicated experiments produced two separate analyses of the same process for replication purposes.

Figure 7A:
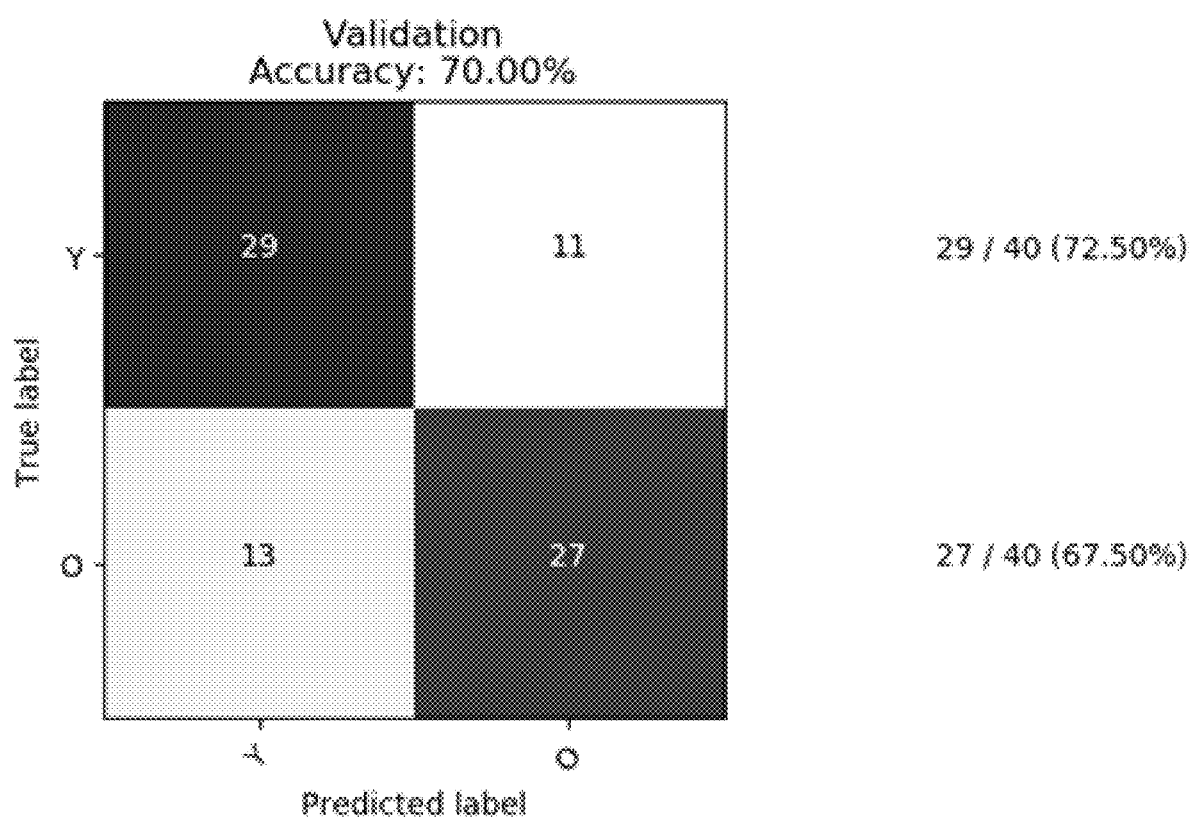
FIG. 7A illustrates an well-aggregated per-tile confusion matrix for an example fold of a biological age prediction by analysis of mouse myoblast cells.
Figure 7B:
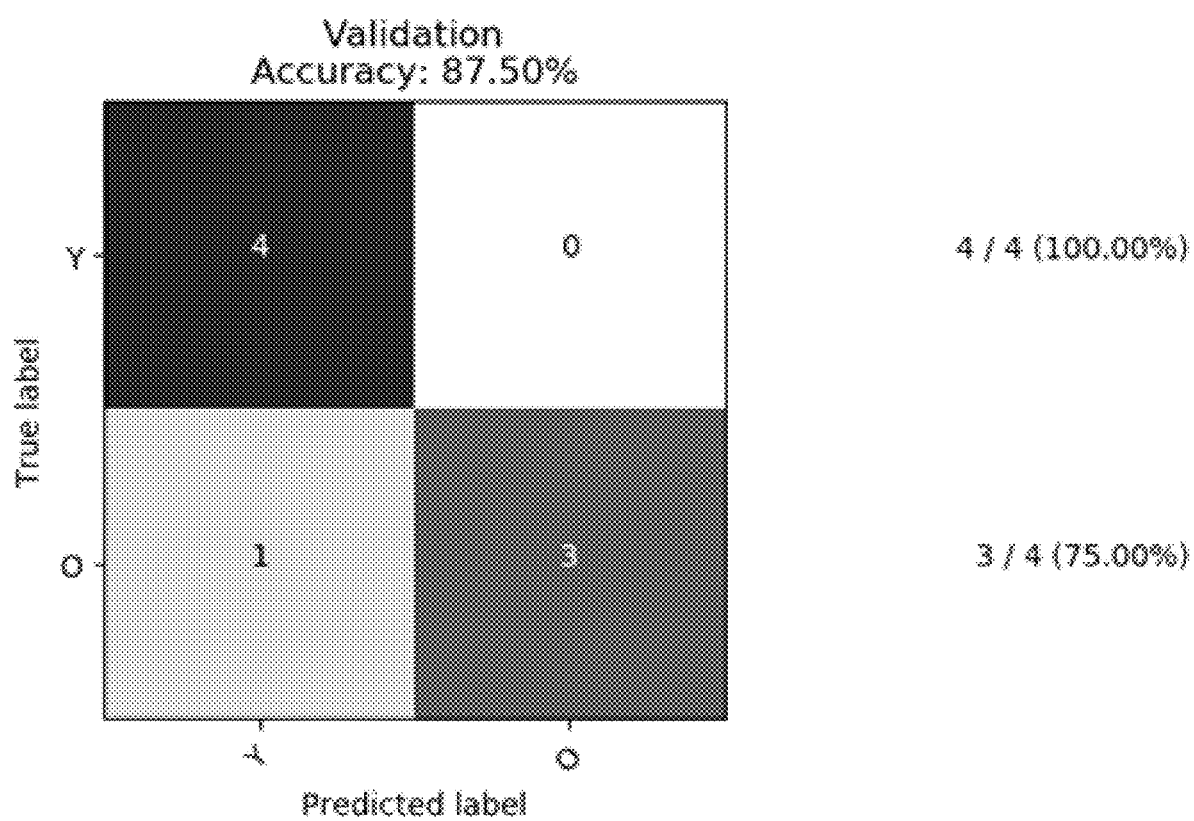
FIG. 7B illustrates a mouse-aggregated confusion matrix for an example fold.
Figure 7C:
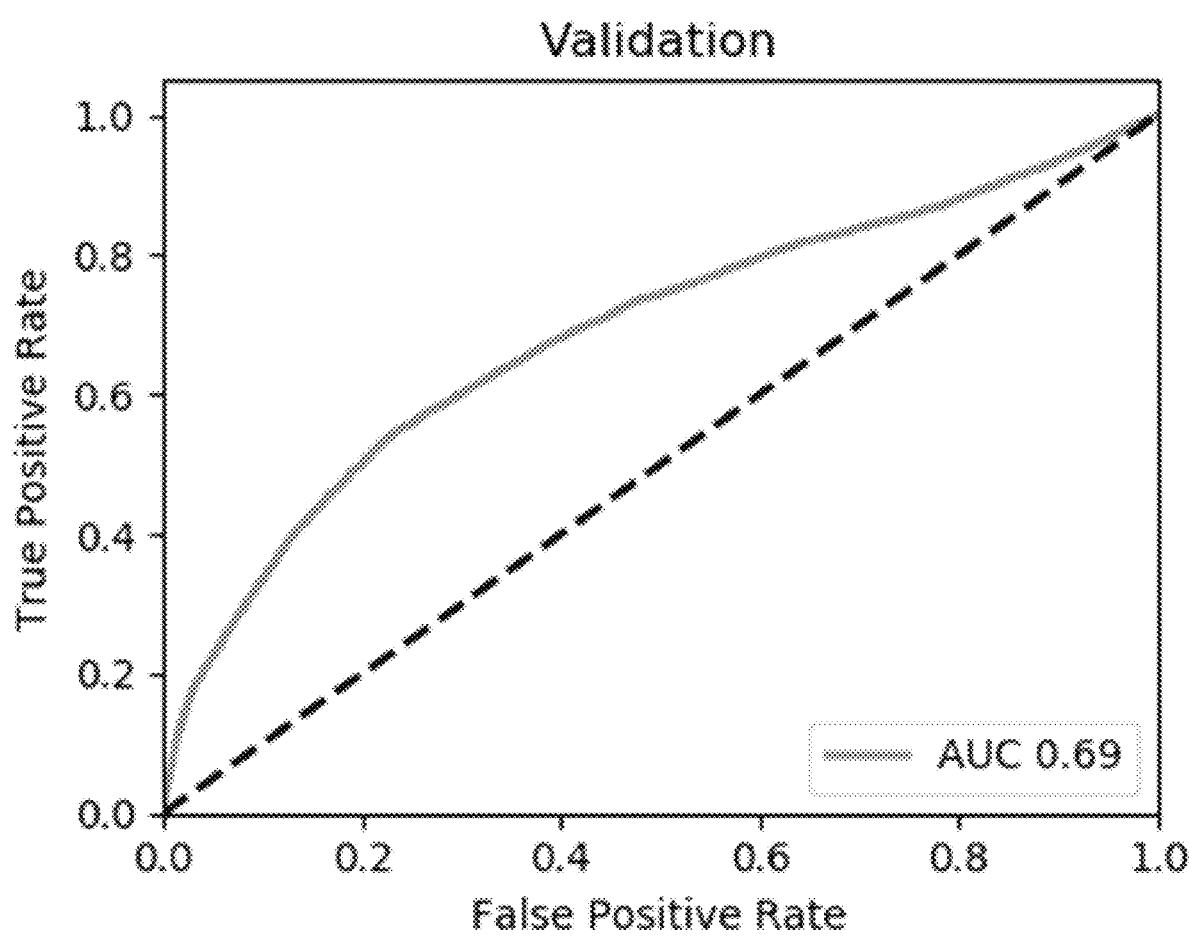
FIG. 7C illustrates an un-aggregated per-image ROC curve for "Y vs. O" classification.

As discussed in Examples 1 and 2, the biological age predictions were produced using a classification system (e.g., predicting age groups) in two different manners (this time using both individual well and aggregated mouse predictions). The results are illustrated in FIGS. 7A-7D using confusion matrices (FIGS. 7A-7B, well-aggregated and mouse-aggregated confusion matrices for "Y vs. O" classification) and an ROC plot (FIG. 7C, un-aggregated per-image prediction). In particular, an AUC value of 0.69 was achieved for the "Y vs. O" classification.

Overall, the biological age of mouse myoblast cells was predicted with excellent results for both individual well and mouse predictions, as shown in Table 3.

TABLE 3

Accuracy of biological age prediction of mouse myoblast cell samples

| Classification type | Well prediction accuracy | Mouse prediction accuracy |
|---|---|---|
| Y vs. O | 72.2% | 79.2% |

Due to the significant biological differences between cell types, culture conditions, and especially different organisms, it may be difficult and not appropriate to directly compare biological age prediction performances between myoblasts and different cell types (e.g., myoblasts vs. fibroblasts vs. keratinocytes). While excellent biological age prediction power was observed for all cell types reported here, due to their natural biological variability it may be expected to find variation in prediction accuracies across cell types.

Example 4

Biological Age Prediction by Analysis of Human Fibroblast Cells

Biological age prediction was performed by analysis of human fibroblast cells.

Cell samples were acquired and prepared as follows. Human dermal fibroblasts from 10 subjects participating in the Baltimore Longitudinal Study of Aging were procured from the Coriell Institute for Medical Research's Biobank repository: 5 young ("Y") samples (age 22 to 28 years old, ID #: AG11747, AG07804, AG09860, AG06310, AG09559) and 5 old ("O") samples (Age 81, ID #: AG09149, AG07802, AG09156, AG13218, AG04055).

Next, images were acquired as follows for testing biological age prediction. A set of 5 lines of human fibroblasts from young donors and 5 lines of human fibroblasts from old donors were individually cultured, stained, and imaged.

All 10 human fibroblast lines were received live in flask in Eagle's MEM with Hank's BSS, with 26 mM Hepes; ambient $CO_2$ with 2 mM L-glutamine. At reception, the cells were switched to DMEM 10% Fetal Bovine Serum (FBS) and cultured until they reached 80% confluency. The cells were then passaged using trypsin and plated in new flasks for another passage in DMEM 10% FBS. At the next passage, the cells were plated in 384-well plates at a density of 1,000 cells per well. Particular attention was made at each step to ensure that any experimenter working with the cells handled both young and old cells at the same time. Again, this step is taken to minimize any experimental bias introduced between young and old samples. The plate layout was also specifically designed to minimize experimental bias caused by the well position in the plate, as described in Example 3. In addition, only 200 wells were used in the 384-well plate layout in order to limit edge effects from the wells on the edge of the plate. Each of the 10 human fibroblast lines were plated in 20 replicate wells, covering all 200 used wells.

At 48 hours post plating, the cells were fixed and stained with Concanavalin A-AF488 (1:10), Mitotracker-Red (250 nM) and Phalloidin-AF647 (1:25) and counterstained with Hoechst 33342 (1:1000).

A high-throughput automated imager was used to capture 100 non-overlapping fields per well (a 10×10 matrix) at a magnification of 40× using a Thermo CX7 automated microscope with a separate image captured for each of our 4 stain channels and brightfield. This image acquisition produced about 100,000 unique non-overlapping field images (2208 pixels wide) per plate (5 channels×200 wells×100 fields per well).

Next, the image data were analyzed according to the approach described in Example 3.

Figure 8A:
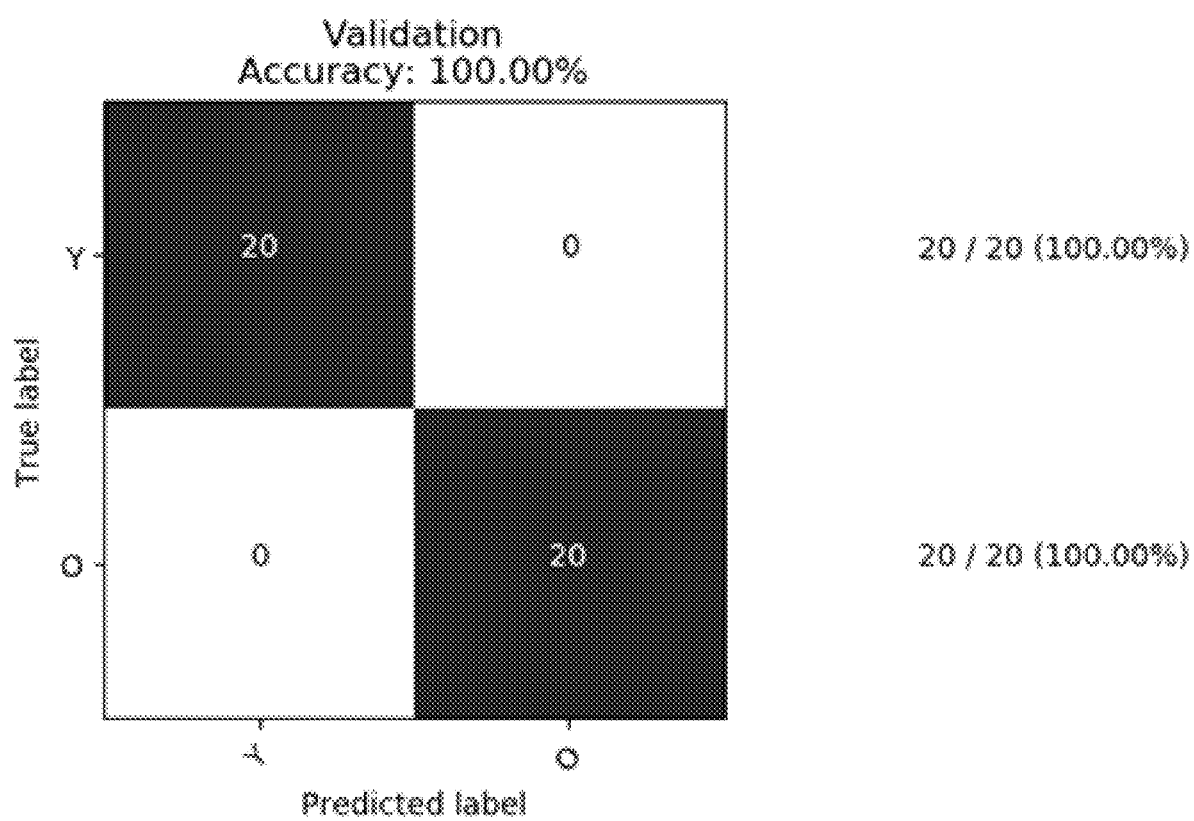
FIG. 8A illustrates an well-aggregated confusion matrix for an example fold of a biological age prediction by analysis of human fibroblast cells.
Figure 8B:
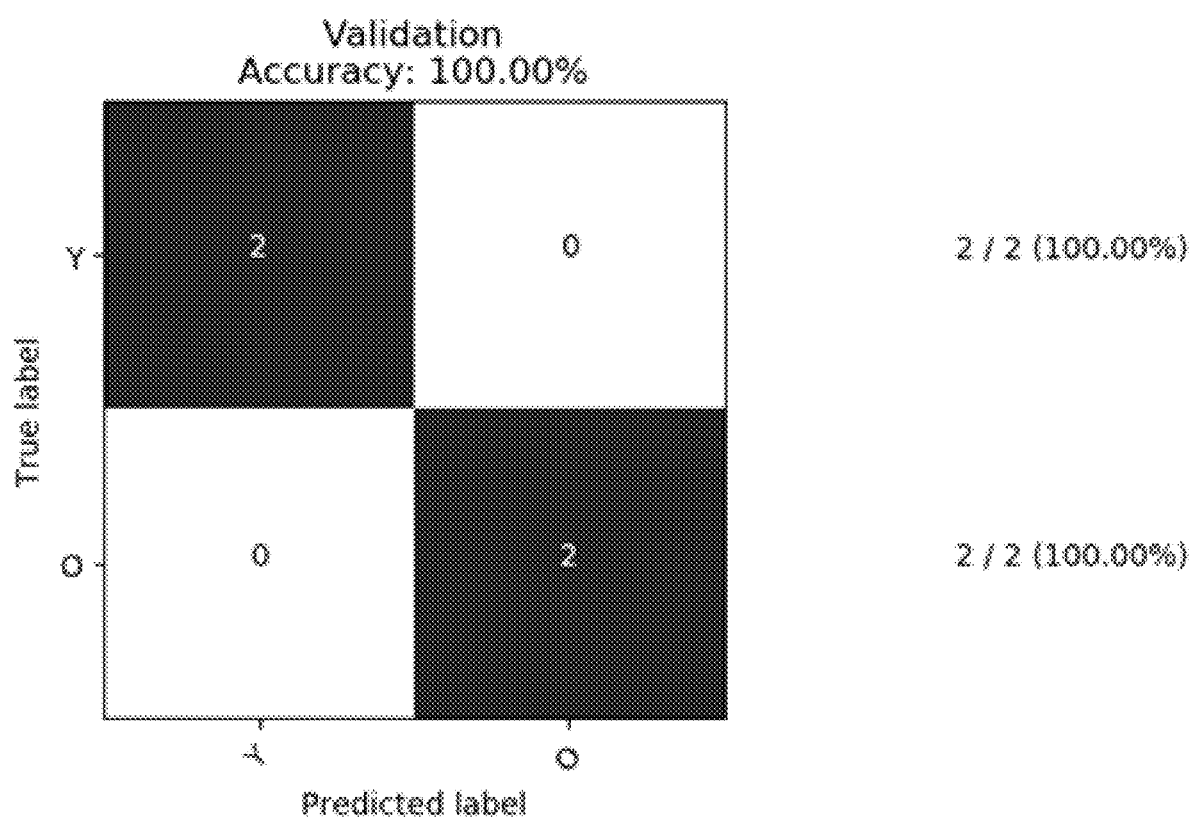
FIG. 8B illustrates a donor-aggregated confusion matrix for an example fold.
Figure 8C:
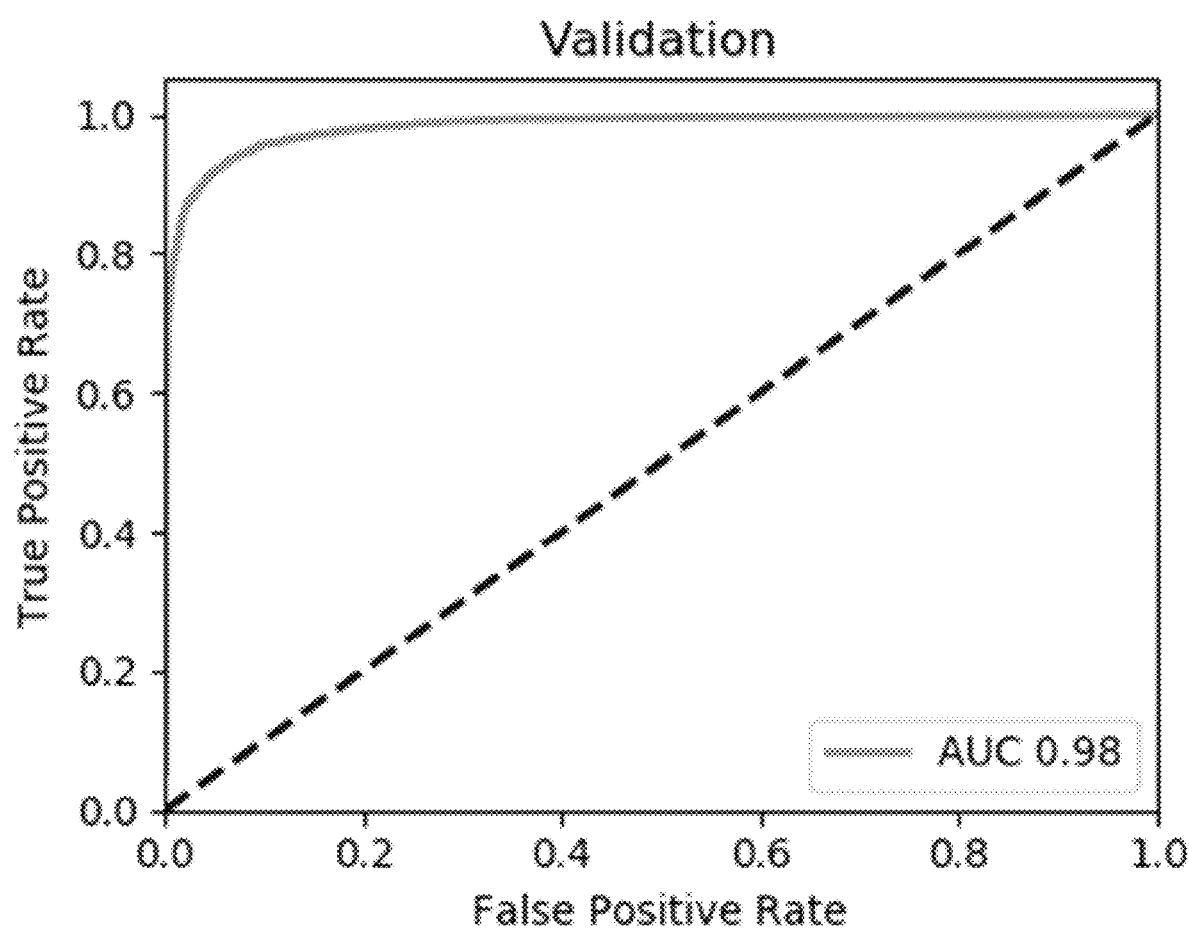
FIG. 8C illustrates an un-aggregated per-image ROC curve for "Y vs. O" classification.

As discussed in Example 3, the biological age predictions were produced using a classification system (e.g., predicting age groups) in two different manners (using both individual well and aggregated donor predictions). The results are illustrated in FIGS. 8A-8C using confusion matrices (FIGS. 8A-8B, well-aggregated and donor-aggregated confusion matrices for "Y vs. O" classification) and an ROC plot (FIG. 8C, un-aggregated per-image prediction). In particular, an AUC value of 0.98 was achieved for the "Y vs. O" classification.

Overall, the biological age of human fibroblast cells was predicted with excellent results for both individual well and donor predictions, as shown in Table 4.

TABLE 4

Accuracy of biological age prediction of human fibroblast cell samples

| Classification type | Well prediction accuracy | Donor prediction accuracy |
|---|---|---|
| Y vs. O | 100% | 100% |

Due to the significant biological differences between cell types, culture conditions, and especially different organisms, it may be difficult and not appropriate to directly compare biological age prediction performances between fibroblasts and different cell types (e.g., myoblasts vs. fibroblasts vs. keratinocytes). While excellent biological age prediction power was observed for all cell types reported here, due to their natural biological variability it may be expected to find significant variations in prediction accuracies across cell types.

Example 5

Biological Age Prediction by Analysis of Human Keratinocyte Cells

Biological age prediction was performed by analysis of human keratinocyte cells.

Cell samples were acquired and prepared as follows.

Ten human keratinocyte lines were purchased from Lonza (Catalog No. 192627). Five young ("Y") keratinocyte samples ranging from 20 to 37 years of age (Lot Nos. 530069, 540810, 549412, 552653, and 577922) and five old ("O") keratinocyte samples ranging from 60 to 88 years of age (Lot Nos. 34015, 30214, 29598, 29549, and 34014) were used.

Next, images were acquired as follows for testing biological age prediction. A set of 5 lines of human keratinocytes from young donors and 5 lines of human keratinocytes from old donors are individually cultured, stained, and imaged.

All 10 keratinocyte lines were received frozen. The cells were thawed and cultured in Gibco defined K-SFM media (Thermo-Fisher Catalog No. 10744019). The cells were passaged using trypsin and plated in 384-well plates at a density of 2500 cells per well. Particular attention was made at each step to ensure that any experimenter working with the cells handled both young and old cells at the same time. Again, this step is taken to minimize any experimental bias introduced between young and old samples. The plate layout was also specifically designed to minimize experimental bias caused by the well position in the plate, as described Example 3. In addition, only 200 wells are used in the 384-well plate layout in order to limit edge effects from the wells on the edge of the plate. Each of the 10 human keratinocyte lines were plated in 20 replicate wells, covering all 200 used wells.

At 72 hours post plating, the cells were fixed and stained with Concanavalin A-AF488 (1:10), Mitotracker-Red (250 nM) and Phalloidin-AF647 (1:25) and counterstained with Hoechst 33342 (1:1000).

A high-throughput automated imager is used to capture 100 non-overlapping fields per well (a 10×10 matrix) at a magnification of 40× using a Thermo CX7 automated microscope with a separate image captured for each of our 4 stain channels and brightfield. This image acquisition produced about 100,000 unique non-overlapping field images (2208 pixels wide) per plate (5 channels×200 wells×100 fields per well).

Next, the image data were analyzed according to the approach described in Example 3.

Figure 9A:
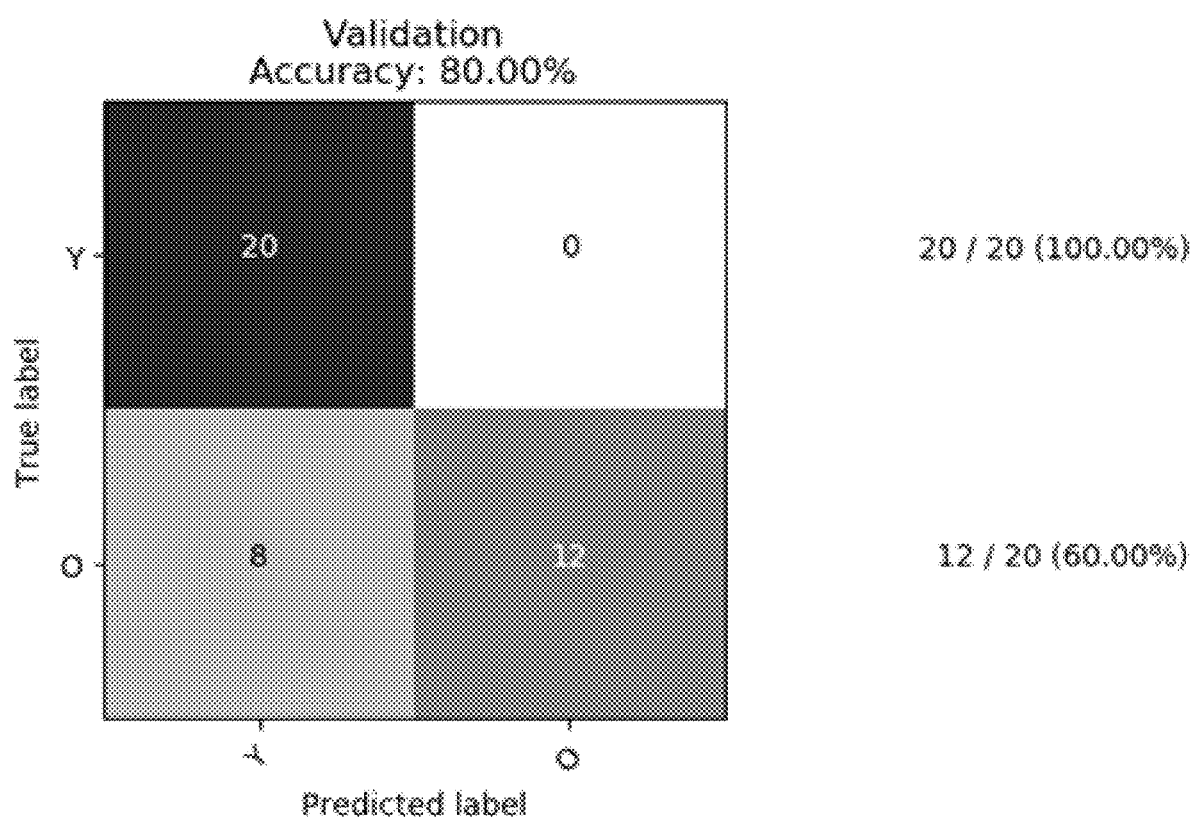
FIG. 9A illustrates an well-aggregated confusion matrix for an example fold of a biological age prediction by analysis of human keratinocyte cells.
Figure 9B:
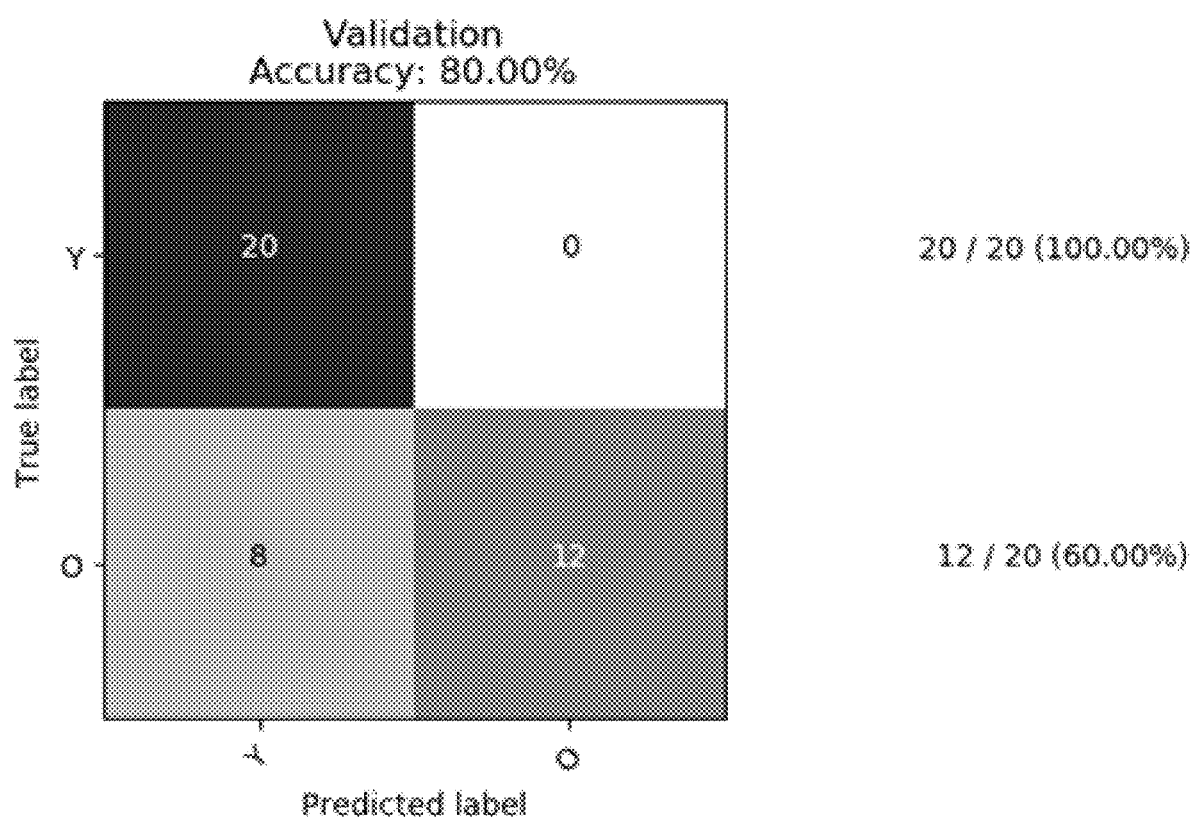
FIG. 9B illustrates a donor-aggregated confusion matrix for an example fold.
Figure 9C:
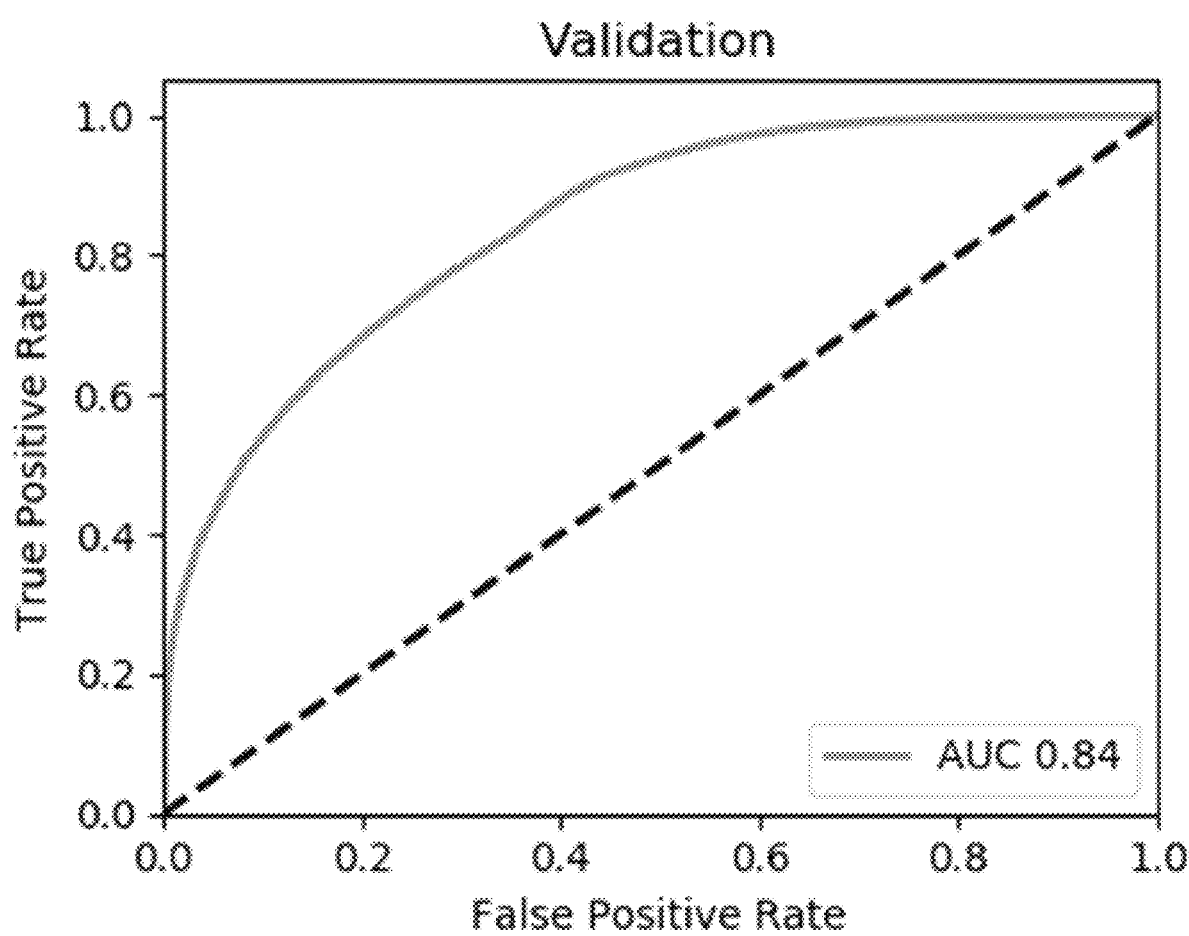
FIG. 9C illustrates an un-aggregated per-image ROC curve for "Y vs. O" classification.

As discussed in Example 4, the biological age predictions were produced using a classification system (e.g., predicting age groups) in two different manners (using both individual well and aggregated donor predictions). The results are illustrated in FIGS. 9A-9C using confusion matrices (FIGS. 9A-9B, well-aggregated and donor-aggregated confusion matrices for "Y vs. O" classification) and an ROC plot (FIG. 9C, un-aggregated per-image prediction). In particular, an AUC value of 0.84 was achieved for the "Y vs. O" classification.

Overall, the biological age of human keratinocyte cells was predicted with excellent results for both individual well and donor predictions, as shown in Table 5.

Biological age of human keratinocyte cells are predicted with promising results for both individual well and donor predictions.

TABLE 5

Accuracy of biological age prediction of human keratinocyte cell samples

| Classification type | Well prediction accuracy | Donor prediction accuracy |
|---|---|---|
| Y vs. O | 80.0% | 75% |

Due to the significant biological differences between cell types, culture conditions, and especially different organisms, it may be difficult and not appropriate to directly compare biological age prediction performances between keratinocytes and different cell types (e.g., myoblasts vs. fibroblasts vs. keratinocytes). While excellent biological age prediction power was observed for all cell types reported here, due to their natural biological variability it may be expected to find significant variations in prediction accuracies across cell types.

Example 6

In Vivo Tissue-Based Drug Screening of Mouse Skin Tissue

The machine learning systems and methods for predicting biological age were applied toward accelerating drug screens designed to detect interventions that slow or reverse one or more phenotypes of aging. Such a drug screening approach was tested using proof-of-concept drug screens, including an in vivo drug screening experimental model. This machine learning-based drug screening approach for aging-related therapies is described below. The machine learning-based skin tissue aging modeling approach was used to test an in vivo screening system for detecting topical anti-aging interventions on mouse skin.

Mouse skin tissue samples were acquired and prepared as follows. Skin samples were collected from 75 healthy C57BL/6J mice in five separate groups: 15 mice in a control group were 10 months old ("Control 1"), 15 mice in another control group were 14 months old ("Control 2"), 15 mice in a third control group were 18 months old ("Control 3"), and two independent treatment groups comprised 18-month-old mice ("Test Article 1" and "Test Article 2"). Each treatment group included 15 mice given a daily topical application for 61 days, as detailed below. All mouse ages are referenced from the start of the experiment.

The mice were shaved as necessary on a weekly basis in order to enable daily topical application on the back of the mice. The topical application was applied in a 2 cm×2 cm square on the back of the mice identified with indelible ink.

Figure 10:
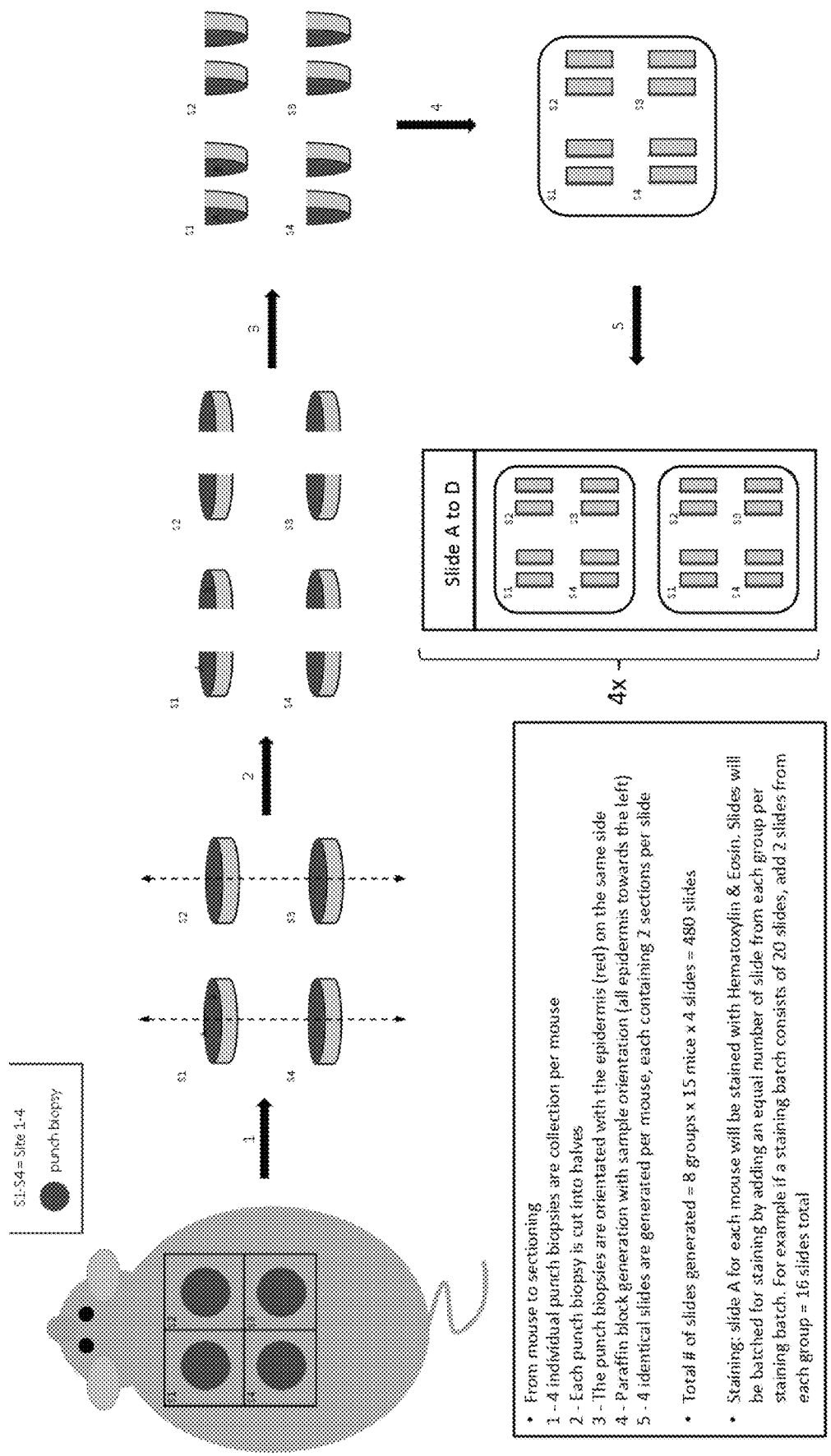
FIG. 10 illustrates an example of a biopsy cutting and slide preparation scheme.

At day 61, four individual 5-mm diameter punch biopsies were collected from the backs of each mouse in a grid in the test article treated area. Biopsies were fixed for 24 to 48 hours in normal buffer formalin 10%. Each biopsy was then cut into two halves, and all eight biopsy pieces were then mounted into a single paraffin block, as illustrated by the biopsy cutting and slide preparation scheme shown in FIG. 10.

Next, sample slides were prepared as follows. Each block was sectioned into slides at a thickness of 5 microns. Each slide contained 16 separate sections of tissues from the same paraffin block.

One slide for each mouse was stained using HES (hematoxylin eosin saffron). Since the process of staining slides may be able to stain only 20 slides at a time, slides were batched into groups of 20, while ensuring that each batch of slides contained balanced representation of slides across all five groups (Controls 1-3 and Test Articles 1-2). This deliberate batching process was performed in order to minimize biases introduced by the per-batch staining process.

Next, images were acquired as follows. Full-resolution digital slide images were acquired for all slides using a high-throughput slide scanner. Images were acquired at a magnification of 40× and a resolution of 0.25 microns per pixel. The slides were scanned in brightfield.

All mice in the Control 1-3 groups received a control topical application comprising 80% DMSO, 19.9% water, and 0.1% Carbopol 934. Each mouse received 60 μL daily applications of this solution applied over the 2 cm×2 cm test site.

Animals in Test Article 1 received a daily dose of 16.2 μg of All Trans Retinoic Acid (ATRA) (CAS No. 302-79-4) dissolved in the same solution as the control groups and applied identically as the control groups.

Animals in Test Article 2 receive a daily dose of a combination of 5.18 mg of Vitamin C (CAS No. 50-81-7) and 1.29 mg of Vitamin E (CAS No. 59-02-9) dissolved in the same solution as the control groups and applied identically as the control groups.

Next, the data were prepared as follows. The images from the control mice comprised the "aging dataset," while the images from the two test articles comprised the "compound dataset." Next, the data were prepared using a similar process as that described in Example 1. First, each whole slide image was segmented into smaller, non-overlapping square tiles of 512 pixels each, and each of the mice's data were partitioned into training and test sets with proportions of ⅔ and ⅓, respectively, while ensuring that no mouse has data appearing in both the training and test sets at the same time. This resulted in an aging dataset of about 5,000 images in the aging dataset and a treatment dataset of about 5,000 images. Analyses were performed as described below, and the average performance across three different training and test folds are reported, unless otherwise specified.

Next, the data was analyzed using a similar deep convolutional neural network architecture and the machine learning analysis approach as that described in Example 1. First, the deep convolutional neural network architecture was trained using the aging dataset and the machine learning analysis approach described in Example 1. Performing this training yields a final set of weights to use with the neural network for the treatment analysis. Second, the effects of the treatments were analyzed by applying the generated neural network to the entirety of the treatment dataset. This is subsequently referred to as a "transference" of the aging model to the treatment data.

Average age predictions for each mouse were produced by predicting the biological age classification for each tile and averaging all tiles' predictions together. This calculation was performed for all three folds of the data, and those average predictions were then averaged together again. This produced a single numerical biological age prediction for each mouse, which was then averaged into a single numerical biological age prediction for the Control group (averaged across control groups 1-3) and each of the Test Article groups, as shown in Table 6.

TABLE 6

Average predicted age and change relative to control group for the control group and both test article groups

|  | Average predicted age (months) | Change relative to control group |
|---|---|---|
| Control group | 17.2 |  |
| Test Article 1 | 15.9 | −7.28% |
| Test Article 2 | 16.9 | −1.23% |

Next, p-values were calculated using the Kolmogorov-Smirnov test to assess the statistical difference of the distributions of age predictions for Test Article groups versus the Control Group. One p-value was calculated for each fold of the machine learning analysis. All three folds were found to be statistically significant for Test Article 1, and two of the three folds were found to be statistically significant for Test Article 2, as shown in Table 7.

TABLE 7 p-values for each of three folds for both test article groups

|  | Fold 1's p-value | Fold 2's p-value | Fold 3's p-value |
|---|---|---|---|
| Test Article 1 | 0.000000 | 0.000000 | 0.001814 |
| Test Article 2 | 0.000006 | 0.122279 | 0.000125 |

Example 7

In Vitro Cell-Based Drug Screening of Mouse Myoblast Cells

The machine learning systems and methods for predicting biological age were applied toward accelerating drug screens designed to detect interventions that slow or reverse one or more phenotypes of aging. Such a drug screening approach was tested using proof-of-concept drug screens, including an in vitro drug screening experimental model. This machine learning-based drug screening approach for aging-related therapies is described below. The machine learning-based mouse myoblast cellular aging approach was used to test an in vitro screening model for detecting anti-aging molecules for myoblasts.

The myoblast cell screening was run in parallel with the myoblast biological age prediction described in Example 3, and the same processes for primary cell acquisition, preparation, processing, and image acquisition steps were performed as described in Example 3.

For myoblast screening, replicate 384-well plates were dedicated to testing compound treatments (Treatment Plates)

and were seeded with primary myoblasts, replicating the same plate layout as the myoblast age prediction experiment described in Example 3.

For the Treatment Plates, after the cells adhere to the plate (around 2 hours post-plating) the media was changed. For each set of 10 replicate wells from each primary myoblast line, 4 of the wells received media supplemented with vehicle control, 3 wells received media supplemented with one test compound, and 3 wells received media supplemented with another test compound. In this manner, each Treatment Plate was used to test two different compounds, and three Treatment Plates were used in total to test six different compounds.

Six different compounds were tested, as shown in Table 8.

TABLE 8

Compounds tested using mouse myoblast cells

| Compound | Concentration |
|---|---|
| Oxytocin | 30 nM |
| TGFbeta | 10 ng/mL |
| Wnt3a | 100 ng/ml |
| Klotho | 0.5 µg/mL |
| ALK5 inhibitor II | 0.5 µM |
| PP242 | 300 nM |

All Treatment Plates were fed 24 hours post-plating with myoblast growth media supplemented with drugs or their respective vehicle control.

As mentioned, the plates are handled, processed, and stained in the same way as described in the myoblast biological age prediction described in Example 3. Briefly, these plates were stained for EdU, desmin, ER cytopainter, and counterstained with Hoechst.

Next, the data were prepared using a similar process as that described in Example 3. This created a treatment dataset that was analyzed using a previously generated aging model, which was trained on the aging dataset that was generated as described in Example 3.

Next, the data was analyzed using a similar deep convolutional neural network architecture and the machine learning analysis approach described in Example 1. First, the deep convolutional neural network architecture was trained using the aging dataset and the machine learning analysis approach described in Example 1. Performing this training yields a final set of weights to use with the neural network for the treatment analysis. Second, the effects of the treatments were analyzed by applying the generated neural network to the entirety of the treatment dataset. This is subsequently referred to as a "transference" of the aging model to the treatment data.

Next, as described in Example 6, average age predictions for each mouse were produced by predicting the biological age classification for each tile and averaging all tiles' predictions together. This calculation was performed for all three folds of the data, and those average predictions were then averaged together again. This produced a single numerical biological age prediction for each mouse, which was compared to control.

Next, as described in Example 6, p-values were calculated using the Kolmogorov-Smirnov test to assess the statistical difference of the distributions of age predictions for each compound versus control. Note that in this case, because there are multiple plates being tested, each with different test compounds, each compound is compared only to the control wells on its own plate, thereby resulting in different control values for each compound, as shown in Table 9.

TABLE 9

Average predicted age of treatment and control groups for each compound

| Compound | Average predicted age of control (months) | Average predicted age of treatment (months) | Change relative to control | p-value |
|---|---|---|---|---|
| Oxytocin | 68.29 | 67.66 | −0.92% | 0.971392 |
| TGFbeta | 68.25 | 53.16 | −22.11% | 0.000000 |
| Wnt3a | 67.51 | 64.11 | −5.04% | 0.001281 |
| Klotho | 64.28 | 64.18 | −0.16% | 0.424582 |
| ALK5 inhibitor II | 65.47 | 56.22 | −14.13% | 0.000266 |
| PP242 | 67.78 | 56.16 | −17.14% | 0.000996 |

Four of the six compounds tested were detected as causing statistically significant reductions in biological age prediction as reported by the machine learning model. These molecules were identified as interesting possible "hits" for further follow-up analysis related to their effect on biological age, thereby validating this approach as a useful in vitro screen that can be deployed for high-throughput detection of promising anti-aging compounds.

Example 8

High-Throughput In Vitro Cell-Based Screening

The myoblast screening results described in Example 7 are deployed as a high-throughput screen (HTS) designed to screen hundreds of thousands of molecules. The approach is quite similar, but the number of cells and wells used to screen those molecules is significantly scaled up.

There may be challenges to overcome when deploying this approach as a high-throughput screen, many of which are related to producing a large enough cell bank of primary cell lines without passaging the cells to an excessive extent such that detected signals of aging are lost.

A high-throughput screen can be performed using the biological age prediction systems and methods of the present disclosure, by performing the following three steps: making a master bank of cells, validating the original biological aging prediction, and performing the actual screen.

Primary myoblast cells are chosen as an illustrative example. However, this technology can be deployed using any of many different cell types, including but not limited to the three cell types described in Examples 3-5 and 7 (myoblasts, fibroblasts, and keratinocytes).

First, a master bank of cells is produced with enough cells to power a high-throughput screen involving many molecules while trying to maintain a low passage number to avoid losing the markers of aging.

Primary myoblast cells are isolated from 49 C57BL/6J mice using the same process as described in Example 3. The vials of cells at passage 1 are thawed and plated at 15,000 cells/cm$^2$ on matrigel-coated flasks, cultured for 63 hours in myoblast growth media, and frozen down at passage 2 into the three populations described below.

Note that care is taken during any freeze or thaw to make sure that all cell lines are frozen and/or thawed at the same time. As described in previous examples, particular attention is made at each step to ensure that any experimenter working with the cells handles both young and old cells at the same time. These steps are taken to minimize any experimental bias introduced between young and old samples.

The cell lines are organized into three distinct populations: (a) 24 separate primary myoblast lines (12 young and 12 old) to be used in reproducing the biological age prediction results ("Individual Young Lines" and "Individual Old Lines"), (b) two mixes, each containing 12 young or old primary cell lines to be used for optional additional machine learning training on each HTS plate ("Young Training Mix" and "Old Training Mix"), and (c) two mixes, each containing 14 primary cell lines to be used for screening molecules ("Young Testing Mix" and "Old Testing Mix"). Each mix is produced with an equal representation of cell counts from each composite cell line.

The limiting factor for an HTS may be the number of vials of Old Testing Mix, as this is the cell population which is used to test many different molecules. The number of vials of Old Testing Mix produced defines the number of molecules available for testing. At the end of this process, 28 vials Old Testing Mix are produced with 5.3M cells per vial, enabling more than about 60,000 molecules to be tested in an initial screen. This process can and is repeated with more cells (and more cell types) to power further screening.

Next, after producing a new master bank of cells to power an HTS, it is important to re-validate the machine learning-powered biological aging prediction process using these cells. This validation is important when testing any new population of cells that have undergone new lab procedures in order to reduce the likelihood that unexpected experimental bias has been introduced.

To perform such validation, all of the Individual Lines and Training Mixes frozen at passage 2 are thawed and plated at 15,000 cells/cm$^2$ on matrigel-coated flasks for 63 hours in myoblast growth media. Then the cells are detached and plated (at passage 3) following the same experimental bias-reducing plate layouts from the myoblast age prediction described in Example 3.

The rest of the culturing, fixation, image acquisition, and analysis process follow the procedures from the myoblast age prediction described in Example 3. To validate the results, the machine learning approach is used on this newly produced population of cells and observed to be at least as successful in predicting biological age when compared to the previous experiments.

Next, the HTS is performed. To run the screen, both the Training Mixes and the Testing Mixes are used. The compounds are tested in wells containing Old Testing Mix. The Young and Old Training Mixes are included in separate wells on each plate in case it is useful to validate the biological age prediction process on each individual plate. The Young Testing Mix is included in separate wells on each plate and includes control molecules used to validate controls' effects on the young mix.

Each plate contains about 300 compounds in Old Testing Mix, each in a single well. The plate also includes 36 other wells with 12 replicates each of Young Training Mix, Old Training Mix, and Young Testing Mix.

All cells are plated in myoblast growth media, and 2 hours later the media is changed as described in the myoblast in vitro screening of Example 7. Each well receives either vehicle control (DMSO) or a screening compound.

In order to screen more than about 60,000 compounds, the HTS is split up into multiple runs, each of which produces 12-15 plates following the plan described above. One vial of Old Testing Mix is used for each run.

Next, image acquisition and analysis are performed. The image acquisition is performed in the same manner described in the myoblast in vitro experiment of Example 7. Analysis and hit detection are also performed in the same manner described in the myoblast in vitro experiment of Example 7.

Next, follow-up is performed after the primary screen. After primary HTS screening, enough vials are maintained to perform standard HTS follow-up experiments: reproducing hits, dose response analysis, etc.

The above HTS procedure is applicable to many cell types, culture procedures, and staining protocols. This can enable unbiased high-throughput screening for age-related phenotype reversal in many different situations.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method comprising:
   (a) obtaining a biological sample;
   (b) obtaining first computer-readable image assay data of said biological sample, said first computer-readable image assay data generated by imaging said biological sample, wherein said first computer-readable image assay data identifies cell morphology or cellular components of said biological sample;
   (c) providing a computer processor programmed with a biological age predictor, wherein said biological age predictor comprises a trained machine learning detection structure configured to receive as inputs computer-readable image assay data generated by imaging test biological samples and to determine as outputs biological ages or ranges of biological ages of said test biological samples, wherein said trained machine learning detection structure is trained using (i) computer-readable image assay data comprising images of training biological samples generated by imaging said training biological samples, wherein said computer-readable image assay data identifies cell morphology or cellular components of said training biological samples, and (ii) biological ages or ranges of biological ages associated with said plurality of training biological samples;
   (d) using said computer processor programmed with said biological age predictor, determining (i) a biological age of said biological sample or (ii) a range of said biological age of said biological sample based on said first computer-readable image assay data;
   (e) contacting said biological sample with a substance, thereby generating a treated biological sample;
   (f) obtaining second computer-readable image assay data of said treated biological sample, said second computer-readable image assay data generated by imaging said treated biological sample, wherein said second computer-readable image assay data identifies cell morphology or cellular components of said treated biological sample; and
   (g) using said computer processor programmed with said biological age predictor, determining (i) a biological age of said treated biological sample or (ii) a range of said biological age of said treated biological sample based on said second computer-readable image assay data.

2. The method of claim 1, wherein said biological sample is a cell sample.

3. The method of claim 2, wherein said cell sample is a skin, muscle, blood, liver, heart, spleen, thymus, brain, myoblast, fibroblast, or keratinocyte cell sample.

4. The method of claim 1, wherein said biological sample is a tissue sample.

5. The method of claim 4, wherein said tissue sample is a skin, fibroblast, muscle, liver, heart, spleen, thymus, or brain tissue sample.

6. The method of claim 1, wherein said trained machine learning detection structure comprises a neural network, a convolutional neural network (CNN), a deep convolutional neural network (DCNN), a cascaded deep convolutional neural network, a simplified CNN, a shallow CNN, or a combination thereof.

7. The method of claim 1, wherein said first computer-readable image assay data or said second computer-readable image assay data identifies biomarkers of said biological sample or said treated biological sample.

8. The method of claim 1, wherein said substance is an anti-aging agent, a drug entity, or an FDA-approved drug entity.

9. The method of claim 1, further comprising determining said biological age of said biological sample, or said biological age of said treated biological sample.

10. The method of claim 1, further comprising determining said range of said biological age of said biological sample, or said range of said biological age of said treated biological sample.

11. A method comprising:
(a) obtaining a biological sample;
(b) performing an image assay on said biological sample to generate computer-readable image assay data of said biological sample, wherein said computer-readable image assay data identifies cell morphology or cellular components of said biological sample;
(c) providing a computer processor programmed with a biological age predictor, wherein said biological age predictor comprises a trained machine learning detection structure configured to receive as inputs computer-readable image assay data generated by imaging test biological samples and to determine as outputs biological ages or ranges of biological ages of said test biological samples, wherein said trained machine learning detection structure is trained using (i) computer-readable image assay data comprising images of training biological samples generated by imaging said training biological samples, wherein said computer-readable image assay data identifies cell morphology or cellular components of said training biological samples, and (ii) biological ages or ranges of biological ages associated with said plurality of training biological samples;
(d) using said computer processor programmed with said biological age predictor, analyzing a set of one or more locations in said computer-readable image assay data to:
(i) identify a feature of said set of one or more locations and classify said feature, and
(ii) determine (i) a biological age of said biological sample or (ii) a range of said biological age of said biological sample based on said identified and classified feature.

12. The method of claim 11, wherein said biological sample is a cell sample.

13. The method of claim 12, wherein said cell sample is a skin, muscle, blood, liver, heart, spleen, thymus, brain, myoblast, fibroblast, or keratinocyte cell sample.

14. The method of claim 11, wherein said biological sample is a tissue sample.

15. The method of claim 14, wherein said tissue sample is a skin, fibroblast, muscle, blood, liver, heart, spleen, thymus, or brain tissue sample.

16. The method of claim 11, wherein said computer-readable image assay data identifies biomarkers of said biological sample.

17. The method of claim 11, further comprising (i) determining said biological age of said biological sample.

18. The method of claim 11, further comprising (ii) determining said range of said biological age of said biological sample.

19. A system comprising: a digital processing device comprising:
(a) a computer processor programmed with a biological age predictor, wherein said biological age predictor comprises a trained machine learning detection structure configured to receive as inputs computer-readable image assay data generated by imaging test biological samples and to determine as outputs biological ages or ranges of biological ages of said test biological samples, wherein said trained machine learning detection structure is trained using (i) computer-readable image assay data comprising images of training biological samples generated by imaging said training biological samples, wherein said computer-readable image assay data identifies cell morphology or cellular components of said training biological samples, and (ii) biological ages or ranges of biological ages associated with said plurality of training biological samples; and
(c) a computer program including instructions executable by said computer processor to create an application comprising:
a biological age assessment module configured to use said biological age predictor to analyze computer-readable image assay data of a biological sample, said computer-readable image assay data generated by imaging said biological sample, wherein said first computer-readable image assay data identifies cell morphology or cellular components of said biological sample, wherein said trained machine learning detection structure of said biological age predictor analyzes a set of one or more locations in said computer-readable image assay data to (1) identify a feature of said set of one or more locations and classify said feature, and (2) determine (i) a biological age of said biological sample or (ii) a range of said biological age of said biological sample based on said identified and classified feature.

20. The system of claim 19, wherein said trained machine learning detection structure comprises a neural network, a convolutional neural network (CNN), a deep convolutional neural network (DCNN), a cascaded deep convolutional neural network, a simplified CNN, a shallow CNN, or a combination thereof.

21. The system of claim 19, wherein said computer-readable image assay data identifies biomarkers of said biological sample.

22. The system of claim 19, wherein said biological age assessment module determines said biological age of said biological sample.

23. The system of claim 19, wherein said biological age assessment module determines said range of said biological age of said biological sample.

24. A method for screening a test compound to identify an anti-aging agent, comprising:
   (a) contacting a biological sample with said test compound, thereby generating a treated biological sample;
   (b) performing an image assay on said treated biological sample to generate computer-readable image assay data of said treated biological sample, wherein said computer-readable image assay data identifies cell morphology or cellular components of said treated biological sample;
   (c) providing a computer processor programmed with a biological age predictor, wherein said biological age predictor comprises a trained machine learning detection structure configured to receive as inputs computer-readable image assay data generated by imaging test biological samples and to determine as outputs biological ages or ranges of biological ages of said test biological samples, wherein said trained machine learning detection structure is trained using (i) computer-readable image assay data comprising images of training biological samples generated by imaging said training biological samples, wherein said computer-readable image assay data identifies cell morphology or cellular components of said training biological samples, and (ii) biological ages or ranges of biological ages associated with said plurality of training biological samples;
   (d) using said computer processor programmed with said biological age predictor, determining (i) a biological age of said treated biological sample or (ii) a range of said biological age of said treated biological sample; and
   (e) identifying said test compound as an anti-aging agent based on (i) said biological age of said treated biological sample or (ii) said range of said biological age of said treated biological sample.

25. The method of claim 1, wherein contacting said biological sample with said substance is performed in vitro.

26. The method of claim 11, wherein said trained machine learning detection structure comprises a neural network, a convolutional neural network (CNN), a deep convolutional neural network (DCNN), a cascaded deep convolutional neural network, a simplified CNN, a shallow CNN, or a combination thereof.

27. The method of claim 26, wherein said trained machine learning detection structure comprises a CNN.

28. The method of claim 24, wherein said trained machine learning detection structure comprises a neural network, a convolutional neural network (CNN), a deep convolutional neural network (DCNN), a cascaded deep convolutional neural network, a simplified CNN, a shallow CNN, or a combination thereof.

29. The method of claim 24, wherein said computer-readable image assay data identifies biomarkers of said treated biological sample.

30. The method of claim 24, wherein contacting said biological sample with said test compound is performed in vitro.

* * * * *

UNITED STATES PATENT AND TRADEMARK OFFICE
CERTIFICATE OF CORRECTION

PATENT NO. : 10,886,008 B2  
APPLICATION NO. : 16/255366  
DATED : January 5, 2021  
INVENTOR(S) : Ben Kamens et al.

Page 1 of 1

It is certified that error appears in the above-identified patent and that said Letters Patent is hereby corrected as shown below:

In the Claims

In Claim 11 at Column 43, Line 57, "samples;" should read --samples; and--.

In Claim 19 at Column 44, Line 37, "(c) a computer program including instructions executable" should read --(b) a computer program including instructions executable--.

In Claim 27 at Column 46, Line 17, "learning detection structure comprises a CNN." should read --learning detection structure comprises said CNN.--.

Signed and Sealed this  
Twenty-third Day of February, 2021

Drew Hirshfeld  
*Performing the Functions and Duties of the  
Under Secretary of Commerce for Intellectual Property and  
Director of the United States Patent and Trademark Office*